United States Patent [19]

Natsugari et al.

[11] Patent Number: 5,189,043
[45] Date of Patent: Feb. 23, 1993

[54] ISOQUINOLONE DERIVATIVES, THEIR PRODUCTION AND USE

[75] Inventors: Hideaki Natsugari, Ashiya; Hitoshi Ikeda, Higashiosaka, both of Japan

[73] Assignee: Takeda Chemical Industries, Ltd., Osaka, Japan

[21] Appl. No.: 603,445

[22] Filed: Oct. 26, 1990

[30] Foreign Application Priority Data

Oct. 27, 1989 [JP] Japan .................................. 1-280602
Mar. 28, 1990 [JP] Japan .................................. 2-80184

[51] Int. Cl.$^5$ .................. A61K 31/47; C07D 217/24
[52] U.S. Cl. ............................ 514/309; 546/141; 549/283; 549/289; 549/290
[58] Field of Search ....................... 546/141; 514/309

[56] References Cited

U.S. PATENT DOCUMENTS 4,988,711  1/1991  Angerbauer et al. ............. 546/144

*Primary Examiner*—C. Warren Ivy
*Assistant Examiner*—James H. Turnipseed
*Attorney, Agent, or Firm*—Wegner, Cantor, Mueller & Player

[57] ABSTRACT

A compound of the formula (I):

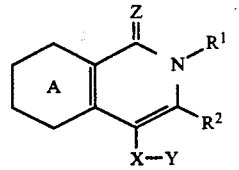

wherein
X is —CH$_2$-CH$_2$— or —CH=CH—,
Y is

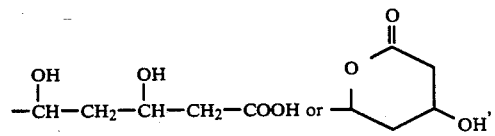

Z is an oxygen or sulfur atom,
R$^1$ and R$^2$ are independently a hydrogen atom, an optionally substituted hydrocarbon group or an optionally substituted heterocyclic group and ring A is an optionally substituted 6-membered homocyclic ring, or its ester or salt which is useful as an inhibitory agent for the biosynthesis of the cholesterol.

7 Claims, No Drawings

ISOQUINOLONE DERIVATIVES, THEIR PRODUCTION AND USE

BACKGROUND OF THE INVENTION

1. Field of the Invention

This invention relates to novel 4-substituted isoquinolone derivatives possessing excellent inhibitory action for 3-hydroxy-3-methylglutaryl CoA (HMG-CoA) reductase, and their production and use.

The compounds of this invention can inhibit the activity of HMG-CoA reductase which is a limiting enzyme for the biosynthesis of cholesterol and then control said biosynthesis of cholesterol, and accordingly are useful as a drug for preventing and/or treating hypercholesterolemia, atherosclerosis related thereto and various diseases caused thereby (e.g., ischemic cardiac diseases such as myocardial infarction, cerebrovascular disturbances such as cerebral infarction, cerebral apoplexy, etc.).

2. Description of the Prior Art

Some lactone derivatives isolated from bacteria or fungi fermentation broths, such as compactin, mevinolin and CS-514 are known as an inhibitor for HMG-CoA reductase [A. Endo, J. Med. Chem. 28, 401 (1985)]. Recently, other synthesized compounds possessing HMG-CoA reductase inhibitory activity, e.g., 3,5-dihydroxy-6-heptenoic (or heptanoic) acids substituted with 6-membered heterocyclic groups at the 7 position have been disclosed in U.S. Pat. No. 4,761,419 (of those substituted with quinoline), European Patent Application Nos. 307,342A and 306,929A (those with pyridine), European Patent Application No. 324347A (those with pyridazine) and European Patent Application No. 308,736A (those with pyrimidine). However, neither chemical synthesis nor HMG-CoA reductase inhibitory activity on isoquinolone compounds substituted with a 3,5-dihydroxy-6-heptenoic (or heptanoic) acid group at the 4 position are reported heretofore.

SUMMARY OF THE INVENTION

This invention provides (1) a novel compound of the formula

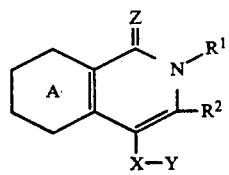

wherein X is —CH$_2$—CH$_2$— or —CH=CH—, Y is

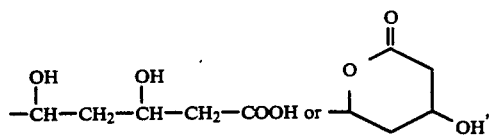

Z is an oxygen or sulfur atom, R$^1$ and R$^2$ independently are each a hydrogen atom, an optionally substituted hydrocarbon group or an optionally substituted heterocyclic group and the ring A is an optionally substituted 6-membered homocyclic ring, its ester or salt;

(2) a process for the production of a compound of the formula (I) or its ester or salt, which comprises reducing a compound of the formula (II)

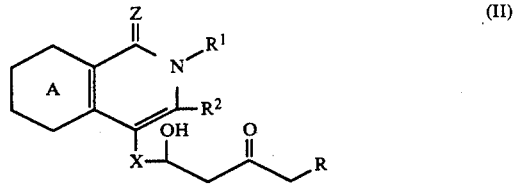

wherein R is an optionally esterified carboxyl group, and R$^1$, R$^2$, X, Z and the ring A have the same meanings as defined above, or its salt to form a compound of the formula (Ia)

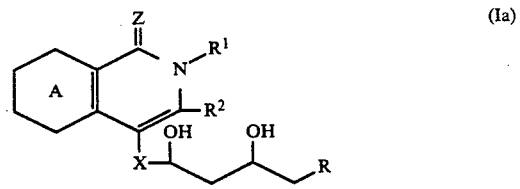

wherein all the symbols are as defined above, and if desired hydrolyzing the compound (Ia) followed by heating preferably in an inert solvent or treating with a dehydrating agent to form a lactone compound of the formula (Ib)

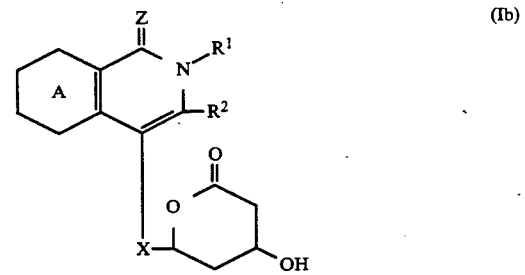

wherein all the symbols are as defined above, or if desired hydrolyzing an ester compound of the formula (Ia) or the lactone compound (Ib) to form a hydroxycarboxylic acid compound of the formula (Ic)

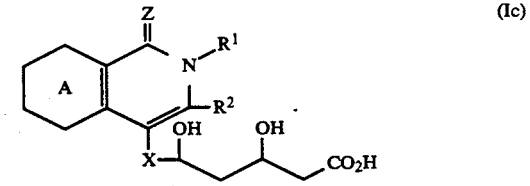

wherein all the symbols are as defined above, or further if desired converting the hydroxycarboxylic acid compound (Ic) into its corresponding salt of the formula (Id)

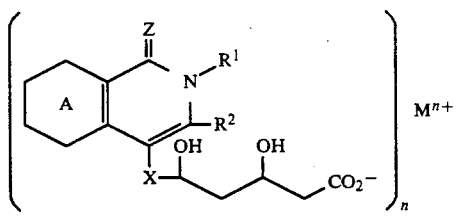

wherein $M^{n+}$ is a cation and the other symbols are as defined above; and (3) an inhibitory agent for the biosynthesis of cholesterol which comprises a compound of the formula (I), or its ester or pharmaceutically acceptable salt and a pharmaceutically acceptable carrier, diluent or excipient.

PREFERRED EMBODIMENT OF THE INVENTION

In the above mentioned formulae, the hydrocarbon group in the optionally substituted hydrocarbon group for $R^1$ and $R^2$ may be an alkyl, cycloalkyl, aryl or alkenyl group. Examples of the alkyl groups are straight or branched chain alkyl groups preferably having 1–10 carbon atoms, such as methyl, ethyl, n-propyl, isopropyl, n-butyl, isobutyl, sec-butyl, t-butyl, 1,1-dimethylpropyl, n-pentyl, isopentyl, n-hexyl, isohexyl, heptyl, octyl, nonanyl and decanyl. Such alkyl groups may possess the same or different one to five, preferably one to three substituents at any position thereof. Examples of the substituents are a halogen, an amino (which may be substituted by an acyl, alkyl, alkenyl, cycloalkyl and/or aryl), cyano, a cycloalkyl, an alkenyl, hydroxyl, an alkoxy (which may be substituted by a halogen, aryl, cycloalkyl and/or alkoxy), an aryl (which may be substituted by a halogen, alkyl, alkoxy, alkylamino, carbamoyl, alkylsulfonyl, cyano, acyloxy and/or aralkyloxy), an aryloxy (which may be substituted by the same group as mentioned in the above aryl), a heterocycle (which may be substituted by an oxo, aryl, alkenylene, halogenoalkyl, alkyl, alkoxy, halogen, carbamoyl and/or cyano), an acyl, an acyloxy, a carbamoyloxy, an alkoxycarbonyloxy, an aralkyl (which may be substituted by an alkyl, alkoxy, halogen and/or cyano), an aralkyloxy (which may be substituted by an acyloxy, alkyl, alkoxy and/or halogen), an alkylsulfonyl, an arylsulfonyl, an alkylsulfonyl, an alkylthio, an arylthio, a heterocycle-thio, (which may be substituted by a cyano, alkyl, halogen and/or oxo), a heterocycle [optionally having a cyano, alkyl, halogen and/or oxo as substituent(s)]-alkylthio, a carboxyl, an alkoxycarbonyl, an aryloxycarbonyl (which may be substituted by an acyloxy, halogen and/or alkoxy), an aminocarbonyl, a mono- or di-alkylaminocarbonyl, a phthalimido and a succinimido.

Examples of the cycloalkyl groups are those preferably having 3–8 carbon atoms, such as cyclopropyl, cyclobutyl, cyclopentyl, cyclohexyl, cycloheptyl and cyclooctyl.

Examples of the aryl groups are phenyl, naphthyl and biphenyl. The aryl group may possess the same or different one to five, preferably one to three substituents at any positions thereof. Examples of the substituents are the same groups as described in the above-mentioned alkyl group or other groups such as a cycloalkyl, alkenyl and alkenylene group.

Examples of the alkenyl groups are those preferably having 2–6 carbon atoms, such as ethylene, allyl, 1,3-butadienyl, 2,4-pentadienyl and 1,3,5-hexatrienyl. The alkenyl group may possess the same substituent(s) as mentioned for the above alkyl group, such as a $C_{1-6}$ alkyl (which may be substituted by the same substituent(s) as mentioned in the above alkyl group), a halogen, an aryl (which may be substituted by a halogen, alkyl and/or alkoxy) and an acyl. The above-mentioned alkenyl group includes isomers with respect to the double bond (i.e., E and Z isomers).

The heterocyclic group for $R_1$ and $R_2$ in the above formulae may be a 5 to 7 membered heterocyclic group containing one sulfur, nitrogen or oxygen atom, a 5 or 6 membered heterocyclic group containing two to four nitrogen atoms, and a 5 or 6 membered heterocyclic group containing one or two nitrogen atoms and one sulfur or oxygen atom. These heterocyclic groups may be condensed with a 6 membered ring containing one or two nitrogen atoms, a benzene ring or a 5 membered ring containing one sulfur atom.

Specifically, the heterocyclic group may be 2-pyridyl, 3-pyridyl, 4-pyridyl, pyrimidinyl, pyrazinyl, pyridazinyl, piperazinyl, pyrazolyl, imidazolyl, thiazolyl, isothiazolyl, oxazolyl, isoxazolyl, quinolyl, tetrazolyl, thiadiazolyl, oxadiazolyl, triazinyl, triazolyl, thienyl, pyrrolyl, furyl, pyrrolidinyl, imidazolidinyl, dithiethanyl, tetrahydropyranyl, tetrahydrofuranyl, benzothienyl, pyranyl, indolyl, isoindolinyl and chromanyl. These heterocyclic groups may possess any number, usually one to six, of substituent. Examples of the substituents are an amino (which may be substituted by an acyl, halogenoalkylacyl, phenyl and/or alkyl), a halogen, nitro, cyano, hydroxyl, carboxyl, oxo, thioxo, a $C_{1-10}$ alkyl (which may be substituted by an aryl, halogen, alkoxy, alkylsulfonyl and/or dialkylamino), a cycloalkyl, an alkoxy, a $C_{1-4}$ acyl, an aryl (which may be substituted by a halogen, alkyl and/or alkoxy), a $C_{1-6}$ alkylthio (which may be substituted by an aryl, halogen, alkoxy, alkylsulfonyl and/or dialkylamino), and a heterocycle (which may be substituted by an alkyl, alkoxy, halogen, nitro, cyano, carboxyl, formyl and/or alkylsulfonyl).

The halogen atom as explained in the substituents includes chlorine, bromine, fluorine and iodine atoms.

The alkyl group as the above-mentioned substituent includes an alkyl having 1–10 carbon atoms, preferably 1–6 carbon atoms, more preferably 1–4 carbon atoms, such as methyl, ethyl, propyl, isopropyl, n-butyl, isobutyl, t-butyl, sec-butyl, pentyl, isopentyl, hexyl, isohexyl, heptyl, octyl, nonyl and decyl.

The cycloalkyl group as the above-mentioned substituent includes those having preferably 3–6 carbon atoms, such as cyclopropyl, cyclobutyl, cyclopentyl and cyclohexyl.

The alkoxy group as the substituent includes those having preferably 1–4 carbon atoms, such as methoxy, ethoxy, n-propoxy, i-propoxy, n-butoxy, i-butoxy and t-butoxy.

The aryl group as the substituent includes phenyl, naphtyl or the like.

The heterocyclic group as the substituent may be the same as exemplified for the above-mentioned heterocyclic group.

The acyl group as the substituent may be one preferably having 1–6 carbon atoms, more preferably having 1–4 carbon atoms, such as formyl, acetyl, propionyl, butyryl, isobutyryl, valeryl, isovaleryl, pivaloyl and hexanoyl. The aralkyl group as the substituent may be benzyl, phenethyl or phenylpropyl.

The alkenyl or alkenylene group as the substituent may be the same as exemplified for the above-mentioned alkenyl group.

The number of substituent for each of the above groups is preferably one to three.

The ring A in the formulae means a 6-membered homocyclic ring consisting of carbon atoms which may be substituted by the same or different one to five, preferably one to three substituents at any positions thereof. Examples of the 6-membered homocyclic rings are

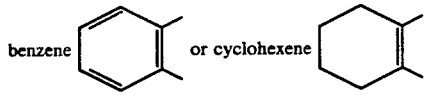

The same substituent as that of the optionally substituted aryl group for $R^1$ and $R^2$ is applicable to the substituent for the ring A.

Examples of the ester residues in the optionally esterfied carboxyl group are an alkyl containing 1 to 4 carbon atoms (e.g., methyl, ethyl, propyl or tert-butyl) and a substituted alkyl (e.g., benzyl, diphenylmethyl, methoxymethyl or 2,2,2-trichloromethyl).

Preferably, the cation for $M^{n+}$ is a pharmaceutically acceptable cation, such as a cation derived from a metal (e.g., sodium, potassium calcium, magnesium, aluminum or zinc) or a cation derived from ammonia or an organic nitrogen-containing base (e.g., triethylamine, piperidine, pyrrolidine or pyridine).

The object compounds of this invention shall be understood to include the compounds of the formulae (Ia), (Ib), (Ic) and (Id).

The hydroxy compound (Ia) can be prepared by reducing the keto compound (II).

The reduction can be conducted by using a reducing agent which can convert carbonyl group to hydroxyl group. Usually, a metal hydride is used in an inert solvent. Examples of the metal hydrides are sodium boron hydride, lithium boron hydride, zinc boron hydride and sodium cyanoboron hydride, among which sodium boron hydride is preferable. The reaction can be preferably conducted in the presence of a trialkylboron such as triethylboron or tri-n-butylboron. The inert solvent may be a lower alkanol such as methanol or ethanol; an ether such as diethyl ether, dioxane or tetrahydrofuran or a hydrocarbon such as benzene or toluene, or a mixture thereof. Preferably, the solvent is a mixture of methanol and tetrahydrofuran. The reaction temperature is usually about $-100°$ C. to 40° C., preferably about $-80°$ C. to 25° C. The amount of the reducing agent to be used is usually about 1 to 2 equivalents preferably 1 to 1.5 equivalents, to the compound (II). The reaction time is usually 10 minutes to 8 hours, depending upon the starting material, reducing agent, reaction temperature and solvent.

Among the resulting compounds (Ia), the carboxylic ester if desired can be converted to the corresponding acid (Ic), lactone (Ib) or salt (Id), and also these compounds are convertible to each other in accordance with conventional methods.

The hydroxycarboxylic acid (Ic) can be prepared by hydrolyzing the carboxylic ester (Ia) or the lactone (Ib) in accordance with conventional methods. Generally, the hydrolysis is conducted by using a base in an inert solvent. Then, the resulting salt of (Ic) is treated with an acid to obtain the free form of (Ic). As for the condition of the hydrolysis, the base may be alkali metal hydroxides or alkali earth metal hydroxides (e.g., sodium hydroxide, potassium hydroxyde, or barium hydroxide), alkali metal carbonates (e.g., sodium carbonate or potassium carbonate) and alkali metal alcoholates (e.g., sodium methoxide, sodium ethoxide, potassium methoxide or potassium ethoxide), among which sodium hydroxide and potassium hydroxide are preferable. The solvents may be water, alcohols (e.g., methanol or ethanol) and ethers (e.g., tetrahydrofuran or dioxane), or a mixture thereof. The amount of the base to be used is usually about 1-3 equivalents, preferably about 1-1.5 equivalents, to the compound (Ia). The reaction temperature is about 0° C. to 100° C., preferably about 10° C. to 40° C. The reaction time is generally about 30 minutes to 6 hours, depending upon the starting material, base, reaction temperature and solvent. This hydrolysis will give a salt of (Ic) with the base's cation as counter ion, which is treated with an acid to isolate the free carboxylic acid (Ic). Usually, an inorganic acid such as hydrochloric acid, hydrobromic acid, phosphoric acid or potassium hydrogen sulfate is used as the acid.

The salt (Id) is produced as an intermediate for the preparation of (Ic) from the above-mentioned (Ia) or (Ib) and can be isolated in accordance with a conventional method. Also, (Ic) can be converted into (Id) by the treatment with a base containing a desired cation in accordance with a conventional method.

The lactone (Ib) can be preferably produced by heating the hydroxycarboxylic acid (Ic) in an anhydrous inert solvent, although it may be sometimes formed by spontaneous cyclization of (Ic). The inert solvent to be used may be hydrocarbons such as benzene, toluene and xylene or ethers such as tetrahydrofuran and dioxane, which may be singly or in a mixture thereof. In some cases, the reaction is preferably conducted by using a catalyst such as a sulfonic acid compound (e.g., p-toluene sulfonic acid or methane sulfonic acid), a carboxylic acid (e.g., acetic acid or trifluoroacetic acid), an inorganic acid (e.g., hydrogen chloride, hydrogen bromide or sulfuric acid) or a Lewis acid (e.g., boron trifluoride ethyl etherate). The amount of such catalyst to be used is about 0.001–0.1 equivalent to the compound (Ic). The reaction temperature is about 50° C. to 200° C., preferably about 70° C. to 150° C. The conversion of (Ic) into (Id) can be also conducted by reacting with a carbodiimide [e.g., dichlohexylcarbodiimide, 1-ethyl-3-(3-dimethylaminopropyl)carbodiimide or 1-cyclohexyl-3-(2-morpholinoethyl)carbodiimide metho-p-toluenesulfonate] in a solvent (e.g., a halogenated hydrocarbon such as methylene chloride or chloroform or an ether such as tetrahydrofuran or dioxane) at 0° C. to 50° C.

The object compounds (I) thus obtained can be isolated and purified by known means, such as concentration, change of basicity, redistribution, extraction by solvent, chromatography, crystallization, recrystallization and freeze-drying.

The object compounds (I) which contain two asymmetric carbon atoms at the moiety of Y have theoretically four kinds of isomers and additionally have two kinds of isomers at a double bond in the case where the moiety of X is —CH=CH—. These isomers and mixtures thereof are included in this invention. Among these isomers, the case where X is —CH=CH— and Y is

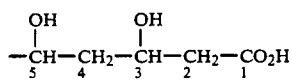

or its ester or salt is preferably 3R,5S-configuration or its racemate (i.e., 3RS,5SR-configuration), and the case where X is as above and Y is

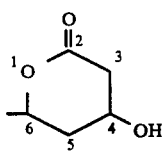

is preferably 4R,6S-configuration or its racemate (i.e., 4RS,6SR-configuration).

Also, the case where X is —CH$_2$CH$_2$— and Y is the above-mentioned chain structure is preferably 3R,5S-configuration or its racemate (i.e., 3RS,5RS-configuration) and the case where X is as above and Y is the above-mentioned lactone structure is preferably in 4R,6R-configuration or its racemate (i.e., 4RS,6RS-configuration). Also, when X is —CH=CH—, E-configuration is preferable.

The compounds (I) and their esters or salts possess an excellent inhibitory action against HMG-CoA reductase. Since HMG-CoA reductase is a limiting enzyme for the biosynthesis of cholesterol, they are an inhibitor for the biosynthesis of cholesterol. Accordingly, the compounds of this invention are useful as a drug for preventing and/or treating hypercholesterolemia, atherosclerosis and diseases caused thereby (e.g., ischemic cardiac disease such as myocardial infarction, cerebrovascular disturbances such as cerebral infarction, cerebral apoplexy, etc.) in mammals (e.g., mouse, rat, hamster, rabbit, cat, dog, horse, cattle, sheep, monkey, human, etc.), and also as a drug for preventing and/or treating infections of fungi such as candidiasis.

When the compound (I) of this invention is used as the above-mentioned drug, it can be administered orally or parenterally in a form of powder, granule, tablet, capsule, injection, etc. which can be prepared by mixing with an optional pharmaceutically acceptable carrier, excipient or diluent. Dosage of the compound (I) depends on the kind of the compound, administration route, condition and age of the patient, etc. For example, when a compound (I) is administered orally to an adult patient having hypercholesterolemia, its daily dose is about 0.005–50 mg, preferably about 0.05–10 mg, per 1 kg of weight of the patient for one day, preferably in 1–3 divided forms.

The compounds (IIa) of X having —CH=CH— and the compounds (IIb) of X having —CH$_2$—CH$_2$— which are used as the starting materials in the above method are novel and can be prepared e.g., by the method of Reaction scheme I

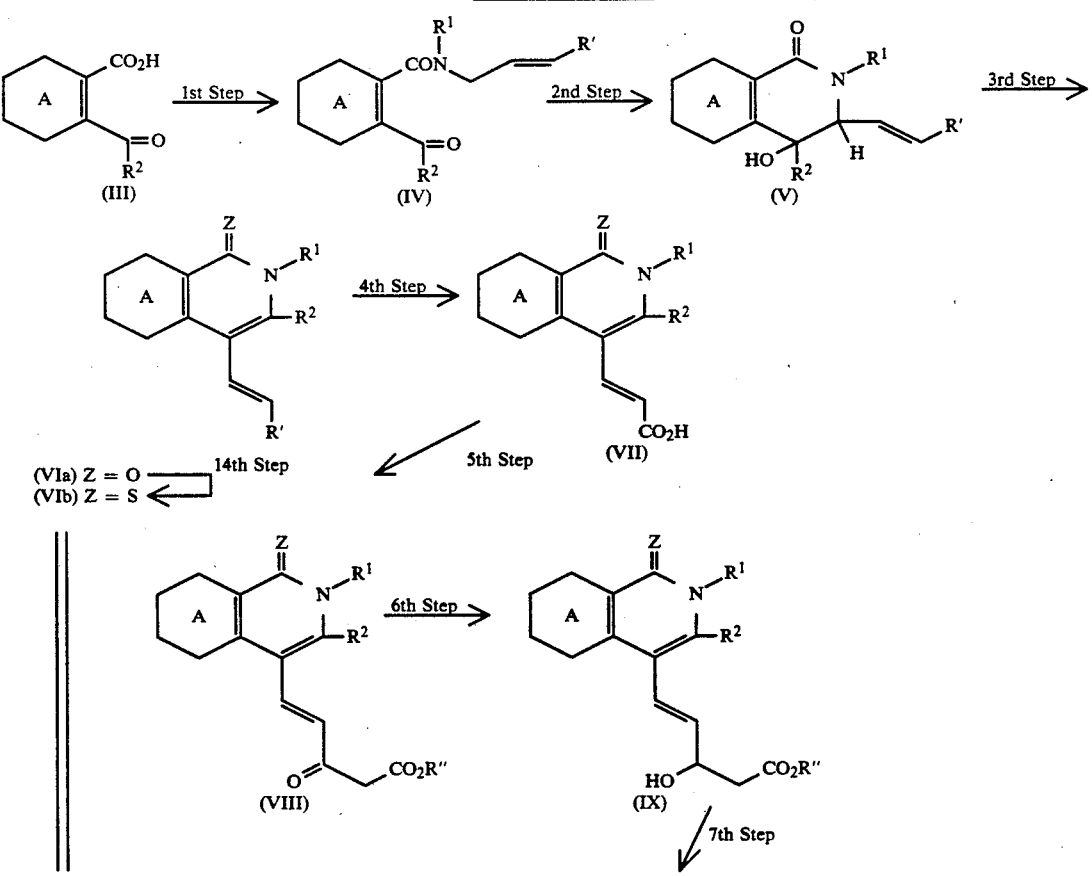

-continued
Reaction Scheme 1

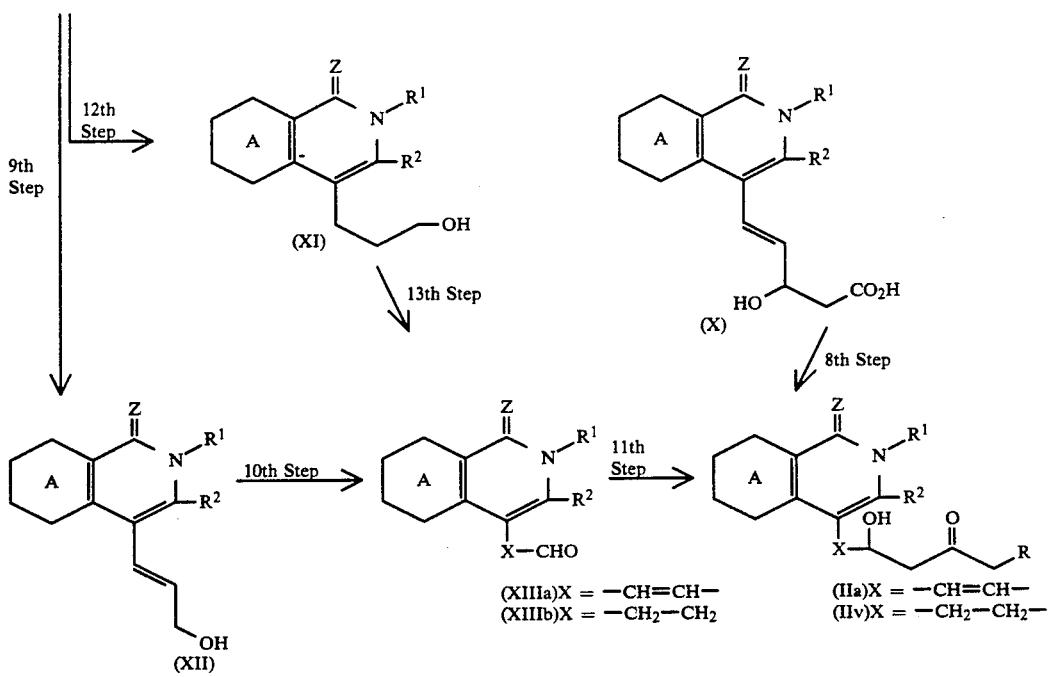

(XII)

In the formula, $R^1$, $R^2$, R, X, Z and the ring A have the same meanings as defined above, R' has the same meaning as R, and R" is a carboxyl-protecting group.

In the above reaction scheme 1, an 2-acylbenzoic acid derivative of the formula (III) is used as the starting material.

The 1st step comprises reacting a compound (III) with a compound (XIV)

$$\underset{HN}{\overset{R^1}{|}}\diagdown\diagup{=}\diagdown R' \qquad (XIV)$$

wherein $R^1$ and R' have the same meanings as above, to convert carboxyl group of (III) into amino group, thereby forming a compound (IV).

In the reaction, the carboxylic acid (III) is usually used as its reactive derivative and reacted with the compound (XIV). Suitable examples of the reactive derivatives are the acid halides, active esters, acid anhydrides, amide compounds and active thioesters. The acid halide such as acid chloride or acid bromide is preferably used. In case of using the acid chloride, the reaction is preferably conducted in the presence of a base. Suitable examples of the bases are aliphatic tertiary amine (e.g., trimethylamine, triethylamine, tripropylamine and tri-n-butylamine), tertiary amines (e.g., N-methylpiperidine, N-methylpyrrolidine, cyclohexyldimethylamine and N-methylmorpholine), dialkylamines (e.g., di-n-butylamine, diisobutylamine and dicyclohexylamine), aromatic amines (e.g., pyridine, lutidine and γ-collidine) and hydroxide or carbonate of alkali metal (e.g., lithium, sodium and potassium) or alkali earth metal (e.g., calcium and magnesium).

The amount of the compound (XIV) to be used is usually about one equivalent to the compound (III). An excess amount of either one of (XIV) and (III) may be used as far as the reaction is not impeded. The base is usually used in an amount sufficient to trap hydrogen halide as by-product but may be used in an excess amount.

The reaction is usually conducted in a solvent. Suitable examples of the solvents are conventional organic solvents such as ethers (e.g., dioxane, tetrahydrofuran, diethyl ether, diisopropyl ether, propylene oxide and butylene oxide); esters (e.g., ethyl acetate and ethyl formate); halogenated hydrocarbons (e.g., chloroform, dichloromethane, 1,2-dichloroethane and 1,1,1-trichloroethane); hydrocarbons (e.g., benzene, toluene and n-hexane); amides (e.g., N,N-dimethylformamide and N,N-dimethylacetamide); or nitriles (e.g., acetonitrile), which can be used in single form or as a mixture thereof. Also, the base in liquid can be served as the solvent. The reaction temperature is usually about −50° C. to 150° C., preferably about −30° C. to 80° C., without limiting thereto. The reaction will take usually several ten minutes to several ten hours, sometimes several multiples of ten days, depending on the starting material, base, reaction temperature and solvent.

The acid halide of (III) can be easily prepared in accordance with a conventional method, e.g., by reacting (III) with a halogenating agent such as thionyl chloride, oxalyl chloride, phosphorus pentachloride or phosphorus tribromide, followed by conventional workup.

The 2nd step comprises treating the compound (IV) with a base to cause an intra-molecular addition reaction, thereby forming a ring-closed compound (V). Preferable examples of the bases to be used in the reaction are organic bases such as 1,5-diazabicyclo[4.3.0]-non-5-en (DBN), 1,8-diazabicyclo [5.4.0]undece-7-en (DBU) and N-benzyltrimethylammonium hydroxide (Triton B) and inorganic bases such as sodium methoxide, sodium ethoxide, sodium hydride, potassium hydride, n-butyllithium and lithium diisopropylamide. The amount of the base to be used is usually about 0.5-20 equivalents, preferably 1-5 equivalents, to the compound (IV). The reaction is usually conducted in the solvent as mentioned in the 1st step. The reaction temperature is usually about −80° C. to 200° C., preferably about −50° C. to 150° C. depending on the kind of base to be used. The reaction time is usually about 10 minutes to 24 hours, depending on the starting material, base, reaction temperature and solvent.

In the 3rd step, the compound (V) is subjected to a rearrangement and dehydration reaction to obtain a 4-substituted isoquinolone derivative (VIa). This reaction is a new rearrangement reaction which is not known in any of published literatures. The reaction is preferably conducted in the presence of an acidic catalyst. Suitable examples of the acidic catalysts are sulfonic acid compounds such as p-toluenesulfonic acid, methanesulfonic acid and trifluoromethanesulfonic acid; carboxylic acid compounds such as acetic acid and trifluoroacetic acid; inorganic acid compounds such as hydrogen chloride, hydrogen bromide and sulfuric acid; and Lewis acid compounds such as boron trifluoride etherate, boron trichloride, boron tribromide, boron triiodide, aluminum chloride, diethylaluminum chloride, triethylaluminum, triisobutylaluminum, titanium tetrachloride, zinc chloride, stannous chloride and stannic chloride. The amount of the acidic catalyst to be used is one equivalent to excess, preferably 1–100 equivalents to the compound (V). The reaction is usually conducted in the solvent as mentioned in the 1st step. When the above acid is a liquid, it can serve as a solvent. The reaction temperature is usually about −10° C. to 200° C., preferably 20° C. to 150° C., which varies depending on the kind of the acidic catalyst. The reaction time is usually about 30 minutes to 24 hours, which varies depending on the kind of the starting material, base, reaction temperature and solvent.

In the 4th step, the compound (VIa) of R' being an esterified carboxyl group is converted into the corresponding compound (VII) of R' being carboxyl group. Depending on the kind of the ester group, the reaction can be conducted by using an appropriate method selected from various known methods [e.g., T. W. Greene, Protective Groups in Organic Synthesis, John Wiley & Sons, New York, 1981, pp. 157–187]. For example, the same method as the reaction under a basic condition used for the conversion of the compound (Ia) or (Ib) to (Ic) is applicable to the compound (VIa) of an ester group being a lower alkyl ester as methyl ester or ethyl ester. The compound (VII) is produced in a salt form with the base's cation as counter ion by the above reaction, which hence is treated with an acid in accordance with a conventional method to isolate the carboxylic acid (VII). Examples of the acid to be used are inorganic acids such as hydrochloric acid, hydrobromic acid, phosphoric acid and potassium hydrogen sulfate.

The 5th step is to activate carboxyl group of the compound (VII) and elongate two carbon atoms to yield a β-keto compound (VIII). The reaction can be conducted by using a known reaction method for elongating carbon chains [e.g., D. W. Brooks, L. D. -L. Lu, and S. Manamune, Angew. Chem. Int. Ed. Engl., 18, 72 (1979)] or analogous methods thereto. For example, the compound (VII) is reacted with a reagent such as 1,1'-carbonyldiimidazole or 1,1'-carbonylbis(2-methylimidazole) in 1–2 equivalent amounts to (VII) in a solvent such as tetrahydrofuran or dimethoxyethane at 0° C. to 50° C. to afford an imidazolide. Then the imidazolide without isolation is reacted with magnesium salt of a malonic acid derivative of the following formula (XV) in 1–3 equivalent amounts to (VII) at 0° C. to 50° C. for 1–48 hours (R"COOCH$_2$COO)$_2$Mg (XV)

wherein R" is a carboxyl-protecting group.

The 6th step is to reduce the carbonyl group of the compound (VIII) to form an alcohol compound (IX). This step can be conducted in a way similar to the above-mentioned conversion of (II) to (Ia), except that a boron compound is not necessarily required. Known protecting groups for carboxyl groups are usable for those of R". For example, ester groups in the esterified carboxyl group of R are applicable. Specifically, suitable protecting groups may be alkyl groups having 1–4 carbon atoms (e.g., methyl, ethyl, propyl and t-butyl) and substituted alkyl groups (e.g., benzyl, diphenylmethyl, methoxymethyl and 2,2,2-trichloromethyl).

The 7th step is to convert an ester group of the compound (IX) to a carboxyl group to form a compound (X). This step can be conducted under the same condition as in the above 4th step.

The 8th step is to activate the carboxyl group of the compound (X) and elongate the two carbon atom chain to form a β-keto compound (IIa). The same condition as in the 5th step is applicable to this step.

The 9th step is to the convert unsaturated carboxylic ester of the compound (VIa) to an allyl alcohol group to form a compound (XII). The reaction is usually conducted by using a reducing agent of a metallic hydride compound (e.g., isobutylaluminum hydride) in a solvent such as an ether (e.g., tetrahydrofuran or dimethoxyethane) or a hydrocarbon (e.g., benzene or toluene). The reaction temperature is usually about −80° C. to 25° C. The compound (XII) can be also prepared by converting the carboxylic acid compound (VII) to the corresponding acid halide or active ester in accordance with a known method and subjecting it to the same reduction as in the 6th step.

The 10th step is to oxidize the alcohol group of the compound (XII) to an aldehyde group to form a compound (XIIIa). The oxidation can be conducted by a method using activated dimethyl sulfoxide as oxidizing agent [e.g., DMSO-(COCl)$_2$ method; A. J. Mancuss, D. S. Brownfain and D. Swern, J. Org. Chem., 44, 4148 (1979); DMSO-pyridine sulfur trioxide method: J. R. Parikh and W. V. E. Doering, J. Am. Chem. Soc., 89, 5505 (1967)], a method using activated manganese dioxide [e.g., E. F. Pratt and J. F. Vande Castle, J. Org. Chem., 26, 2973 (1961)] or an analogous method thereto.

The compound (XIIIa) can be also prepared directly from the compound (VIa) or (VII) by using an appropriate reducing agent. For example, the compound (VII) is converted to its acid halide, which is then reduced by tetrakis (triphenylphosphine) palladium (O) or tributyltin hydride.

The 11th step comprises adding an acetoacetic acid moiety to the aldehyde group of the compound (XIIIa) to obtain the compound (IIa). The reaction is conducted by using sodium lithium dianion of acetoacetic ester in accordance with a known method [e.g., G. A. Kraus and P. Gottshalk, J. Org. Chem., 48, 2111 (1983)] or a method analogous thereto. For instance, acetoacetic ester is reacted with sodium hydride and n-butyllithium in tetrahydrofuran to form the dianion, which is then reacted with the aldehyde compound (XIIIa). The reaction is usually conducted at about −80° C. to 25° C.

The 12th step is the reduction of the unsaturated carboxyl (or ester) group of the compound (VIa) to a saturated alcohol group to obtain a compound (XI). The reaction can be conducted by a known method using sodium borohydridelithium chloride [e.g., Y. Hamada and J. Shioiri, Chem. Pharm. Bull., 30, 1921 (1982)] or a method analogous thereto. For instance, the compound (VIa) is reacted with sodium borohydridelithium chloride in 3-10 equivalent amount to (VIa) in a mix solvent of tetrahydrofuran and ethanol at about 10° C. to 80° C.

The 13th step is the oxidation of the alcohol group of the compound (XI) to an aldehyde group to obtain a compound (XIIIb), to which the same condition as in the 10th step is applicable. The resulting compound (XIIIb) can be converted into the compound (IIb) in the same way as in the 11th step.

The 14th step is the conversion of the oxo group of the compound (VIa) to the thioxo group to obtain a compound (VIb). This step is conducted by reacting the compound (VIa) with a thioating agent for the converting amido group to a thioamido group, e.g., a compound containing sulfur and phosphorus such as phosphorus pentasulfide, 2,4-bismethylthio-1,3-dithia-2,4-diphosphetane-2,4-disulfide, 2,4-bis(4-phenoxyphenyl)-1,3-dithio-2,4-diphosphetane-2,4-disulfide, 2,4-bis(4-phenylthiophenyl)-1,3-dithio-2,4-diphosphetane-2,4-disulfide and 2,4-bis(4-methoxyphenyl)-1,3-dithia-2,4-diphosphetane-2,4-disulfide. The amount of the thioating agent to be used is 0.5-20 equivalents, preferably 0.5-10 equivalents to the compound (VIa). The reaction is usually conducted in a solvent. The solvents as mentioned in the 1st step and organic bases such as pyridine are usable. The reaction temperature is usually about 10° C. to 200° C., preferably about 10° C. to 150° C., depending on the kind and amount of the thioating agent. The reaction time is usually about an hour to 24 hours, depending on the starting material, thioating agent, reaction temperature and solvent. The compound (VIb) of Z being S can be prepared by this step. When the same thioation as in this step is applied for the above-mentioned compound (XI, Z=0) or compound (XII, Z=0), it can be converted to the corresponding compound of Z being S. The compound (IIa or IIb) of Z being S can be also prepared from the above thioated compound (XI or XII, Z=S) in accordance with the same method as in the preparation of the compound (IIa or IIb) of Z being 0.

The compounds (VIa) and (XIIIa) as the intermediates described in the reaction scheme 1 can be also prepared by the reaction scheme 2.

Reaction Scheme 2

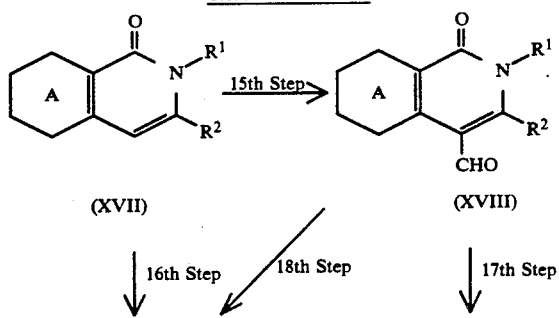

-continued
Reaction Scheme 2

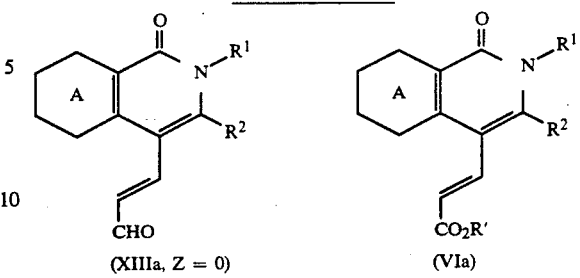

In the formula, $R^1$, $R^2$, $R'$ and the ring A have the same meaning as above.

In the method shown by the reaction scheme 2, an 1-(2H)-isoquinoline derivative (XVII) is used as the starting material.

The 15th step is the introduction of a formyl group to the 4th position of the compound (XVII) to yield a compound (XVIII). This step can be achieved in accordance with a reaction called Vilsmeier-Haack's reaction [A. Vilsmeier and A. Haack, Chem. Ber., 60, 119 (1927) (original report); H. Eilingsfeld, M. Seefelder and H. Weidinger, Angew. Chem., 72, 836 (1960) (general discussion)]. In this reaction, the compound (XVII) is reacted with Vilsmeier's reagent prepared from a N,N-disubstituted formamide (e.g., N,N-dimethylformamide or N-methylformanilide) and an acid halide (e.g., phosphorus oxychloride, phosphorus pentachloride, phosgene or thionyl chloride) in an inert solvent (e.g., acetonitrile, tetrahydrofuran, dichloromethane, chloroform, benzene or toluene). The reaction temperature for preparing Vilsmeir's reagent is usually −10° C. to 35° C., preferably 0° C. to 10° C., and the subsequent reaction of this reagent with the compound (XVII) is usually 20° C. to 120° C., preferably 60° C. to 100° C. The amount of Vilsmeier's reagent to be used is usually 1-20 equivalents, preferably 1-10 equivalents, to the (XVII). The reaction time is usually 1-48 hours, depending on the starting material, reagent, reaction temperature and solvent.

The 16th Step is the introduction of the β-unsaturated aldehyde group of 4th the position of the compound (VII) to form the compound (XIIIa). The same type of reaction (Vilsmeier type reaction) as in the 15th step is applicable to this step. That is, it can be conducted by using a 3-N,N- disubstituted aminoacrolein [e.g., 3-N,N-dimethylamino- acrolein or 3-(N-methyl-N-phenylamino)acrolein] instead of the N,N-disubstituted formamide in the same way as in the 15th step.

The 17th step is the conversion of the aldehyde group of the compound (XVIII) to α,β-unsaturated carboxylic ester group to form the compound (VIa). This step can be generally achieved in accordance with a Wittig reaction or its variant reaction (Horner-Wittig reaction). [e.g., A. W. Johnson, "Ylid Chemistry", Academic Press, New York & London, 1966 (general discussion)]. This reaction is conducted by using an organic phosphonium salt having a group appropriate for the conversion to the compound (VIa) [e.g., triphenylcarbomethyoxy (or ethoxy) methylphosphonium bromide] or an organic phosphorus diester having the above-mentioned group [e.g., carbomethoxy (or ethoxy) methyldiethylphosphonate or carbomethoxy (or ethoxy) methyldimethylphosphonate] in the presence of a base (e.g., sodium hydride, sodium amide, potassium t-butoxide, sodium hydroxide, sodium carbonate, sodium ethoxide, triethylamine or pyridine). The amount of the above reagent to be used is usually 1-10 equivalents, preferably 1-3 equivalents to the compound (XVII). The reaction is usually conducted in an inert solvent (e.g., ethanol, diethyl ether, tetrahydrofuran, benzene, toluene, dimethylformamide or dimethyl sulfoxide). The reaction temperature is usually −80° C. to about the boiling point of the solvent used, preferably −30° C. to 100° C. The reaction time is usually 0.5 to 20 hours, depending on the starting material, reaction temperature and solvent.

The 18th step is the conversion of the aldehyde group of the compound (XVIII) to an α,β-unsaturated aldehyde group to form a compound (XIIIa). The same type of reaction as in the 17th step (Wittig type reaction) is used for this step. In this step, an organic phosphonium salt or phosphorus diester having a group appropriate for the conversion to the compound (XIIIa) is used instead of those in the 17th step. For example, diethyl 2-(cyclohexylimino)phosphonate [W. Nagata & Y. Hayase, J. Chem. Soc., (C), 1969, 460] is reacted with the compound (XVIII) under the same condition as in the 17th step and the resulting enamine of (XIIIa) is hydrolyzed by an acid (e.g., diluted hydrochloric acid or oxalic acid) to obtain the compound (XIIIa).

The compounds obtained by each of the above 1-18 steps can be purified and isolated by known methods such as concentration, change of pH, phase transfer, extraction by solvent, column chromatography, crystallization and recrystallization, but may be directly used to next steps as they are.

The starting material (III) in the reaction scheme 1 can be synthesized by a known method [e.g., P. Aeberli, P. Eden, J. H. Gogerty, W. J. Houlihan, and C. Penberthy, J. Med. Chem., 18, 177 (1976); J. Gronowska and H. M. Mokhtar, Tetrahedron, 38, 1657 (1982)] or methods analogous thereto. The other starting material (XIV) can be synthesized by reacting a 4-halogenocrotonic ester with an amine of the formula (XVI)

R¹NH₂

(R¹ has the same meaning as above) in accordance with a conventional method.

The starting material (XVI) in the reaction scheme 2 can be prepared by various known methods. For instance, it can be obtained by reacting a 1H-2-benzopyran-1-on of the formula (XIX)

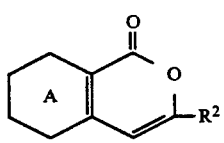
(XIX)

(the symbols are as defined above) [see, R. O. Barry, Chem. Rev., 64, 229 (1964)] with an amine of the formula (XVI) in accordance with a known method [e.g., L. Legrand and N. Lozac'h, Bull. Soc. Chem., 1966, 3828; A. Rose and N. P. Buu-Hoi, J. Chem. Soc., 1968, 2205; D. W. Brown, S. F. Dyke, M. Sainsbury and G. Hardy, J. Chem. Soc., 1971, 3219; B. K. Sarkhel and J. N. Srivastava, Indian J. Chem., 16B, 1034 (1978)], or methods analogous thereto.

Among the object compounds (I), those having 3R,5S-configuration in case of Y being

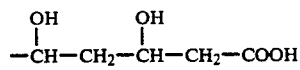

and those having 4R,6S-configuration in case of Y being

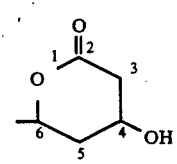

can be prepared e.g., by using an optically active compound (XXIII). The compound (XXIII) can be prepared from an aldehyde compound (XIIIa) in accordance with the reaction scheme 3.

Reaction Scheme 3

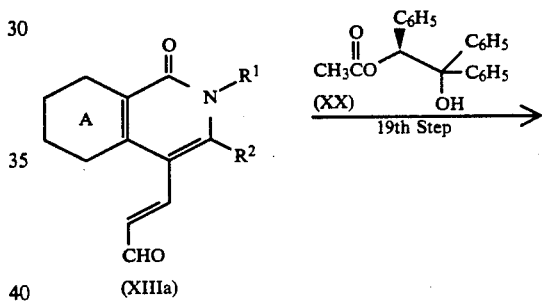

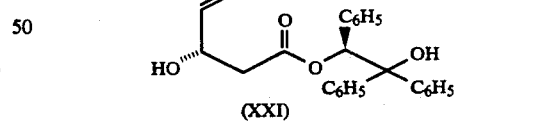

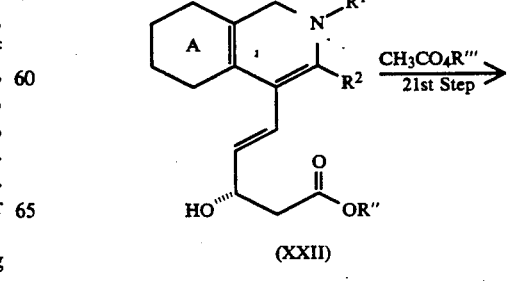

-continued
Reaction Scheme 3

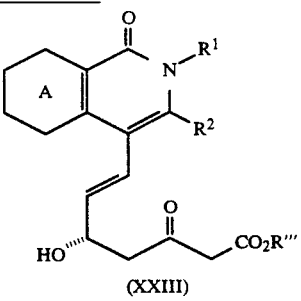

(XXIII)

The 19th step allows to react the aldehyde group of the compound (XIIIa) with an anion of the compound (XX) [(S)-(−)-2-acetoxy-1,1,2-triphenylethanol], to prepare an optically active alcohol compound (XXI). The reaction can be conducted in accordance with a known method[e.g., R. Devant, V. Mahler & M. Braun, Chem. Ber., 121, 397–406 (1988)] or methods analogous thereto. For example, the compound (XX) is treated with 2–2.5 equivalent amounts of a base (e.g., lithium diisopropylamide) in an inert solvent (e.g., tetrahydrofuran) to produce the dianion of (XX), which is then reacted with (XIIIa) usually at about −100° C. to 10° C. Besides, the compound (XX) can be synthesized from (S)-(+) mandelic acid in accordance with a known method (e.g., R. Devant et al. literature as mentioned above).

The 20th step is the ester exchange of the compound (XXI) to form the compound (XXII). The reaction is usually conducted by using a base (e.g., alcoholates such as sodium methoxide and sodium ethoxide) in a solvent (e.g., alcohols such as methanol and ethanol) at about −30° C. to 30° C.

The 21st step is the addition of an 31 acetic acid moiety to an ester group of the compoud (XXII) to form the compound (XXIII). In this step, an acetic acid ester (e.g., methyl acetate, ethyl acetate or t-butyl acetate) is treated with a base (e.g., lithium diisopropylamide) in an inert solvent (e.g., tetrahydrofuran) to form an anion, which is then reacted with the compound (XXII) usually at about −80° C. to 30° C. The compound (XXIII) can be also prepared from the compound (XXII) in accordance with the methods as in the 7th and 8th steps of the reaction scheme 1. Further, the method of the 21st step can be also applicable to the production of the compound (IIa) from the compound (IX) as explained by the 7th and 8th steps of the reaction scheme 1.

The compounds of this invention were evaluated by the following biological method.

Inhibitory action for HMG-CoA reductase of rat's liver microsome

5% cholestyramine diet was fed to male Sprague-Dawley rats (300–400 g of body weight) for 5 days. Activity for HMG-CoA reductase of liver microsome was measured by a variant of the method of Shapiro et al [Biochem. Biophys. Acta 370, 36(1974)]. In this method, the enzyme activity is determined by measuring the formation of $^{14}C$-mevalonate from a substrate $[3^{14}C]$-HMG-CoA in the presence of NADPH. $^{14}C$-Mevalonate is converted into its lactone which can be isolated by silica gel thin layer chromatography developing with benzene: acetone (50:50).

In order to measure inhibitory action for HMG-CoA reductase, test compound was dissolved in dimethyl sulfoxide and the solution was diluted with a buffer solution (100 mM phosphate buffer, 20 mM EDTA.2Na, 10M dithioethritol).

The resulting mixture was incubated with microsome (120 μg protein) at 30° C. for 15 minutes, and further incubated at 37° C. for 30 minutes after addition of d,l-[3-$^{14}C$]-HMG-CoA (0.5 mM, 5000 dpm/nmol) and NADPH (20 mM).

Table 1 shows inhibition rates (%) of representative compounds of this invention and mevinolin as control compound (Merck Co), at $10^{-6}M$.

TABLE 1

| Example No. | Inhibition (%) |
|---|---|
| Mevinolin (control) | 75.5 |
| 1-2 | 92.0 |
| 2-2 | 91.2 |
| 5-2 | 90.4 |
| 10-2 | 90.4 |
| 11-2 | 90.9 |
| 13-1 | 89.6 |
| 13-2 | 95.1 |
| 14-1 | 91.1 |
| 14-2 | 94.0 |
| 15-1 | 94.2 |
| 15-2 | 96.1 |
| 16-1 | 94.2 |
| 16-2 | 96.2 |
| 17-1 | 93.4 |
| 17-2 | 95.8 |
| 18-1 | 90.7 |
| 18-2 | 96.5 |
| 19-2 | 88.0 |
| 21-1 | 91.3 |
| 21-2 | 95.0 |
| 24-2 | 89.6 |
| 32-2 | 89.6 |
| 33-2 | 95.7 |
| 34-2 | 89.6 |
| 35-2 | 96.9 |
| 36-2 | 93.2 |
| 37-2 | 96.2 |
| 38-2 | 95.9 |
| 39-2 | 91.7 |
| 40-2 | 92.6 |
| 41-2 | 88.2 |
| 42-2 | 94.1 |
| 43-2 | 90.6 |
| 47-2 | 93.3 |
| 48-2 | 96.6 |
| 49-2 | 97.1 |
| 49-3 | 92.5 |

As is clear from Table 1, the compounds of the invention show unexpectedly potent inhibitory action against HMG-CoA reductase in comparison with known mevinolin.

EXAMPLES AND REFERENCE EXAMPLES

This invention is illustrated in further detail in the reference examples and examples, which are only examples, and do not limit this invention. Modifications within the scope of this invention are permissible.

Elution in a column chromatography in the reference examples and examples was conducted while monitoring with TLC (Thin Layer Chromatography). In the TLC monitoring, the TLC plate used was 60F$_{254}$ manufactured by Merck Co., the developing solvent was the same as the one used for eluting in the column chromatography, and the detection was conducted with a UV detector. The silica gel for the column was silica gel 60 manufactured by Merck Co., (70–230 mesh).

Further, room temperature means 15°–35° C.

Abbreviations used in the reference examples and examples have the following meanings.

J: coupling constant
Hz: hertz
s: singlet
d: doublet
t: triplet
q: quartet
m: multiplet
b: broad

REFERENCE EXAMPLE I

Ethyl 4-isopropylaminocrotonate

Ethyl 4-bromocrotonate (25.0 g) was added dropwise to a solution of isopropylamine (7.7 g) and triethylamine (13.2 g) in ethanol (200 ml) at room temperature under stirring and taking an hour. The mixture was stirred for 5.5 hours at room temperature. After removing the solvent, to the residue was added ethyl acetate, and the mixture was extracted with 1N hydrochloric acid. Ethyl acetate was added to the hydrochloric acid layer, and alkalified by addition of potassium carbonate powder. After removing the separated oily substance, the ethyl acetate layer was taken out, and the aqueous layer was extracted with ethyl acetate. The combined ethyl acetate layers were washed with saturated sodium chloride solution, dried over anhydrous sodium sulfate and distilled to remove the solvent to give the title compound (14.6 g) as pale yellow oily substance.

NMR (90 MHz, CDCl$_3$)ppm: 1.05(6H,d,J=7 Hz), 1.27(3H,t,J=7 Hz), 2.83(1H,m), 3.38(2H,dd,J=6, 2 Hz), 4.18(2H,q,J=7 Hz), 5.96(1H,dt,J=16, 2 Hz), 6.98(1H,dt,J=16, 6 Hz).

REFERENCE EXAMPLE II

Ethyl 4-n-propylaminocrotonate

Ethyl 4-bromocrotonate (21.4 g) was added dropwise to a solution of n-propylamine (11.8 g) and triethylamine (20.2 g) in ethanol (80 ml) at 0° C. under stirring and taking 1.5 hours, followed by stirring for 0.5 hours at room temperature. After removing the solvent, to the residue was added ethyl acetate, and the mixture was extracted with 1N hydrochloric acid. The extract was alkalified with potassium carbonate powder and extracted with ethyl acetate. The extract was washed with water, dried over anhydrous sodium sulfate and distilled to remove the solvent to give 13.5 of the title compound as pale yellow oily substance.

NMR (200 MHz, CDCl$_3$)ppm: 0.93(3H,t,J=7 Hz), 1.29(3H,t,J=7 Hz), 1.34–1.72(2H, m), 2.45–2.68(2H,m), 3.42(2H,dd,J=5, 2 Hz), 4.20 (2H,q,J=7 Hz), 5.97(1H,d), 6.92–7.08(1H,m).

REFERENCE EXAMPLE III-1

3-(4-Fluorophenyl)-1H-2-benzopyran-1-one

In an atmosphere of argon gas, a solution of n-butyllithium in n-hexane (1.6M, 137 ml) was added to a solution of N,N,N'N'-tetramethylethylenediamine (25.5 g) in anhydrous tetrahydrofuran (100 ml) at −78° C. under stirring and taking 20 minutes, followed by stirring for 20 minutes the same temperature. To the solution was added a solution of N,N-diethyl-2-methylbenzamide (30.0 g) in anhydrous tetrahydrofuran (100 ml) at −78° C. under stirring and taking 30 minutes, followed by stirring for 45 minutes at the same temperature. Further, to the solution was added a solution of 4-fluorobenzaldehyde (21.6 g) in anhydrous tetrahydrofuran (60 ml) at −78° C. taking 30 minutes. The mixture was stirred for 30 minutes at −78° C. and then for 30 minutes at room temperature. An aqueous saturated ammonium chloride solution was added to the reaction mixture, followed by stirring for 10 minutes at room temperature. The mixture was extracted with ethyl acetate. The extract was washed with water, 1N hydrochloric acid and water in turn, dried over anhydrous sodium sulfate and distilled to remove the solvent, thereby affording N,N-diethyl-2-[2'-(4-fluorophenyl)-2'-hydroxyethyl]benzamide as oily substance.

To a solution of this compound in acetone (500 ml) was added Jones' reagent (8N, 22 ml) at 0° C. under stirring, followed by stirring at 0° C. for 15 minutes. Isopropyl alcohol (22 ml) was added to the reaction mixture and stirred at 0° C. for 10 minutes. After removing the solvent, water was added to the residue. The mixture was extracted with ethyl acetate. The extract was washed with water, dried over anhydrous magnesium sulfate and distilled to remove the solvent, thereby affording N,N-diethyl-2-(4-fluorobenzoylmethyl)benzamide as oily substance.

To a solution of this compound in acetic acid (200 ml) was added conc. hydrochloric acid (200 ml) and the mixture was refluxed for 7 hours. After cooling, water was added to the reaction mixture. The mixture was extracted with ethyl acetate. The extract was washed with aqueous sodium hydrogen carbonate and water, dried over anhydrous magnesium sulfate and distilled to remove the solvent, thereby affording 21.6 g of the title compound as colorless crystals. mp. 134°–135° C. (recrystallized from diethyl ether)

IR$\nu_{max}^{Nujol}$cm$^{-1}$: 1720, 1630, 1595, 1305, 1225, 1150, 1060.

NMR (200 MHz, CDCl$_3$)ppm: 6.90(1H,s), 7.10–7.25(2H,m), 7.45–7.60(2H,m), 7.65–7.95(3H,m), 8.31(1H,d,J=7.4 Hz).

Elemental Analysis for C$_{15}$H$_9$O$_2$F: Calculated: C, 75.00; H, 3.78. Found: C, 74.82; H, 3.78.

REFERENCE EXAMPLE III-2

Substituted-1H-2-benzopyran-1ones (J-2~J-6) were obtained by the same method as in Reference Example III-1 (Table 2).

TABLE 2

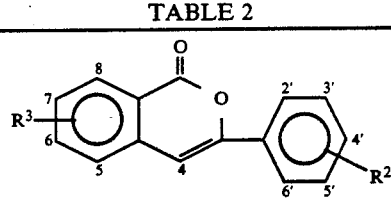

| Compound No. | R$^2$ | R$^3$ | mp(°C.) |
|---|---|---|---|
| J-2 | 4'-F | 5-Me | 161–164 |
| J-3 | " | 5-F | 198 |
| J-4 | " | 5-Cl | 221–222 |
| J-5 | " | 5-MeO | 165–166 |
| J-6 | 4'-Me | H | 110–112* |

*the value in the literature of [A. Ruhemann, Chem. Ber., 24, 3964 (1891)]: mp 116° C.

REFERENCE EXAMPLE IV-STEP 1

3-(4-Fluorophenyl)-2-(1-methylethyl)-1-(2H)-isoquinoline

The compound (1.24 g) obtained by Reference Example III-1 was reacted with isopropylamine (20 g) and treated in the same method as in Step 1 of Reference Example 13 to give 0.72 g of the title compound as colorless crystals. mp 154°-156° C. (from diethyl ether)

IR$\nu_{max}^{Nujol}$cm$^{-1}$: 1640, 1615, 1590, 1550, 1265, 1210, 1070.

NMR (200 MHz, CDCl$_3$)ppm: 1.57(6H,d,J=6.8 Hz), 4.17(1H,m), 6.32(1H,s), 7.10–7.70(7H,m), 8.41(1H,d,J=6.8 Hz).

Elemental Analysis for C$_{18}$H$_{16}$NOF: Calculated: C, 76.85; H, 5.73; N, 4.98. Found: C, 76.78; H, 5.80; N, 4.95.

REFERENCE EXAMPLE IV-STEP 2

1,2-Dihydro-3-(4-fluorophenyl)-2-(1-methylethyl)-1-oxoisoquinoline-4-carboxaldhyde Phosphorus oxychloride (3 ml) was added slowly to dimethylformamide (10 ml) at 0° C. To the solution was added the compound (651 mg) obtained by Step 1 of Reference Example IV, followed by stirring 1.5 hours at 80° C. The reaction mixture was added to ice water, stirred for 15 minutes at room temperature and extracted with ethyl acetate. The extract was washed with aqueous sodium carbonate and water, dried over anhydrous magnesium sulfate and distilled to remove the solvent, thereby affording 293 mg of the title compound as colorless crystals. mp 169°-171° C.

IR$\nu_{max}^{Nujol}$cm$^{-1}$: 1660, 1640, 1595, 1480, 1320, 1255, 1225, 1165.

NMR (200 MHz, CDCl$_3$)ppm: 1.55(6H,d,J=7 Hz), 4.05(1H,m), 7.22–7.48(4H,m), 7.52–7.64(1H,m), 7.70–7.84(1H,m), 8.45(1H,dd, J=8.1 Hz), 9.13(1H,d,J=8 Hz), 9.37(1H,s).

Elemental Analysis for C$_{19}$H$_{16}$NO$_2$F: Calculated: C, 73.77; H, 5.21; N, 4.53. Found: C, 74.04; H, 5.20; N, 4.53.

REFERENCE EXAMPLE IV-STEP 3

Methyl (E)-[1,2-dihydro-3-(4-fluorophenyl)-2-(1-methylethyl)-1-oxo-4-isoquinolinyl]-2-propenoate A solution of the compound (228 mg) obtained by Step 2 of Reference Example IV and methyl triphenylphosphoranylideneacetate (500 mg) in toluene (15 ml) was refluxed for 3 hours. After removing the solvent, the residue was subjected to a silica gel column chromatography, eluting with ethyl acetate-n-hexane to give 216 mg of the title compound as colorless crystals. mp 233°-234° C.

IR$\nu_{max}^{Nujol}$cm$^{-1}$: 1700, 1640, 1595, 1505, 1275, 1220, 1190, 1170.

NMR (200 MHz, CDCl$_3$)ppm: 1.53(6H,d,J=7 Hz), 3.71(3H,s), 4.03(1H,m), 5.96 (1H,d,J=16 Hz), 7.10–7.40(5H,m), 7.48–7.75(2H,m), 7.88(1H,d,J=8 Hz), 8.51(1H,d,J=8 Hz).

REFERENCE EXAMPLE IV-STEP 4

(E)-3-[1,2-Dihydro-3-(4-fluorophenyl)-2-(1-methylethyl)-1-oxo-4-isoquinolinyl]-3-propenoic acid The compound obtained by Step 3 of Reference Example IV was reacted in methanol and treated, in the same way as in Step 4 of Reference Example 1 to give the title compound as colorless crystals. mp 237°-238° C. (from ethyl acetate)

The data of IR and NMR of this product were identical with that of the compound obtained in Step 4 of Reference Example 2.

REFERENCE EXAMPLE 1

Methyl (E)-7-[1,2-dihydro-3-(4-fluoro-2-methoxyphenyl)-2-(1-methylethyl)-1-oxo-4-isoquinolinyl]-5-hydroxy-3-oxo-6-heptenoate Step 1: Ethyl 4-{N-[2-7(4-fluoro-2-methoxybenzoyl)benzoyl]-N-isopropylaminocrotonate}

Thionyl chloride (1.5 ml) was added to a solution of 2-(4-fluoro-2-methoxybenzoyl)benzoic acid (mp 119°-120° C.) (3.66 g) and pyridine (0.03 ml) in benzene (50 ml), followed by refluxing for an hour. The solvent was distilled off to give 2-(4-fluoro-2-methoxybenzoyl)-benzoyl chloride (IR$\nu_{max}^{Nujol}$: 1795 cm$^{-1}$). A solution of this product in methylene chloride (40 ml) was added to a solution of ethyl 4-isopropylaminocrotonate (Reference Example I) (3.6 g) and triethylamine (3.0 ml) in methylene chloride (40 ml), followed by stirring at room temperature for 16 hours. After removing the solvent, ethyl acetate was added to the residue. The mixture was washed with water, dil. hydrochloric acid, water, sodium hydrogen carbonate solution and water in turn. The ethyl acetate layer was dried over anhydrous sodium sulfate and distilled to give the title compound (5.50 g) as pale brown oily substance.

IR$\nu_{max}^{Neat}$cm$^{-1}$: 1720, 1660–1580, 1500, 1460, 1405, 1370, 1340, 1272.

NMR(90 MHz, CDCl$_3$)ppm: 1.17(3H,d,J=7 Hz), 1.25(3H,d,J=7 Hz), 1.27(3H,t,J=7 Hz), 3.70(3H,s), 3.85–4.25(3H,m), 4.20(2H,q,J=7 Hz), 5.73, 6.03(total 1H, each. d, J=16 Hz), 6.6–7.6(8H,m).

Step 2: Ethyl (E)-3-[4-(4-fluoro-2-methoxyphenyl)-4-hydroxy-2-(1-methylethyl)-1-oxo-1,2,3,4-tetrahydro-3-isoquinolinyl]-2-propenoate 1,8-Diazabicyclo[5.4.0]undec-7-ene (DBU) (5.4 ml) was added to a suspension of the compound (5.40 g) obtained by Step 1 in anhydrous toluene (150 ml). The mixture was refluxed for 0.5 hour with stirring. The solvent was distilled off, and to the residue was added ethyl acetate. The solution was washed with aqueous potassium hydrogen sulfate solution and water in turn. The ethyl acetate layer was dried over anhydrous sodium sulfate and distilled to give the title compound (3.60 g) as colorless crystals. mp 178°-179° C. (from ethyl acetate-diethyl ether)

IR$\nu_{max}^{Nujol}$cm$^{-1}$: 3400, 1720, 1630, 1600, 1330.

NMR(90 MHz, CDCl$_3$)ppm: 0.42(3H,d,J=7 Hz), 1.01(3H,d,J=7 Hz), 1.21(3H,t,J=7 Hz), 1.63(1H,b), 4.10(3H,s), 4.10(2H,q,J=7 Hz), 4.73(1H,s), 4.79(1H,m), 5.88(1H,d,J=16 Hz), 6.1–7.6(7H,m), 8.12(1H,d,J=8 Hz).

Elemental Analysis for C$_{24}$H$_{26}$NO$_5$F: Calculated: C, 67.43; H, 6.13; N, 3.28. Found: C, 67.61; H, 6.23; N, 3.24.

Step 3: Ethyl (E)-3-[1,2-dihydro-3-(4-fluoro-2-methoxyphenyl)-2-(1-methylethyl)-1-oxo-4-isoquinolinyl]-2-propenoate A solution of the compound (75 mg) obtained by Step 2 in toluene (2 ml) was added to a solution of boron trifluoride ethyl etherate (1 ml) in toluene (3 ml) at 110° C. under stirring and taking 30 minutes, followed by stirring for 30 minutes as such. After cooling, ethyl acetate was added to the reaction mixture. The mixture was washed with sodium hydrogen carbonate solution and water, dried over anhydrous sodium sulfate and distilled to remove the solvent. The title compound was obtained as pale yellow oily substance (70 mg) (a mixture of the title compound and ethyl (E)-3-[1,2-dihydro-4-(4-fluoro-2-methoxyphenyl)-2-(1-methylethyl)-1-oxo-3-isoquinolinyl]-2-propenoate (about 2:1)].

IR$\nu_{max}^{Neat}$cm$^{-1}$: 1720, 1650, 1600, 1500, 1480, 1450, 1405, 1360, 1325, 1300, 1280, 1175.

NMR(200 MzH, CDCl$_3$)ppm: 1.25, 1.26(total 3H, each t, J=7 Hz), 1.46, 1.59 (each 2H,d,J=6.8 Hz), 1.68, 1.69(each 1H,d,J=6, 8 Hz), 3.71(1H,s), 3.79(2H,s), 3.99(0.67H, m), 4.16(2H,q,J=7 Hz), 4.51(0.33H,m), 5.73(0.33H,d,J=16.0 Hz), 5.96(0.67H,d,J=16.2 Hz), 6.65–7.88(7H,m), 8.48(1H,m).

EI-MS m/z: 409 (M+).

Step 4:
(E)-3-[1,2-Dihydro-3-(4-fluoro-2-methoxyphenyl)-2-(1-methylethyl)-1-oxo-4-isoquinolinyl]-2-propenoic acid 1N Sodium hydroxide solution (13 ml) was added to a solution of the compound (3.00 g) obtained by Step 3 in ethanol (70 ml) at room temperature under stirring. The reaction mixture was stirred at room temperature for 18 hours, and the solvent was distilled off. Water was added to the residue which was washed with ethyl acetate. The aqueous layer was acidified with aqueous potassium hydrogen sulfate solution and extracted with ethyl acetate. The extract was washed with water, dried over anhydrous sodium sulfate and distilled to remove the solvent to give the title compound (1.85 g) as colorless crystals. mp 265°–267° C. (from ethyl acetate-diethyl ether)

IR$\nu_{max}^{Nujol}$cm$^{-1}$: 3450, 1675, 1635, 1600, 1500, 1330, 1295, 1280, 1235.

NMR(400 MHz, CDCl$_3$)ppm: 1.460(3H,d,J=6.8 Hz), 1.585(3H,d,J=6.8 Hz), 3.799 (3H,s), 3.986(1H,septet.J=6.8 Hz), 5.946(1H,d,J=16.1 Hz), 6.763(1H,dd,J=10.5, 2.4 Hz), 6.799(1H,dt, J=8.3, 8.3, 2.4 Hz), 7.072(1H,dd,J=8.3, 6.4 Hz), 7.343(1H,d,J=16.1 Hz), 7.536(1H,ddd,J=8.3, 7.1, 1.3 Hz), 7.678(1H,ddd,J=8.5, 7.3, 1.5 Hz), 7.857(1H,d,J=8.1 Hz), 8.507(1H,dd,J=8.3, 1.0 Hz).

Elemental Analysis for C$_{22}$H$_{20}$NO$_4$F: Calculated: C, 69.28; H, 5.29; N, 3.67. Found: C, 68.99; H, 5.19; N, 3.64.

(E)-3-[1,2-dihydro-4-(4-fluoro-2-methoxyphenyl)-2-(1-methylethyl)-1-oxo-3-isoquinolinyl]-2-propenoic acid (0.85 g) was obtained as pale yellow foam from the mother liquor from which the title compound was taken.

NMR(400 MHz, CDCl$_3$)ppm: 1.684(3H,d,J=6.6 Hz), 1.694(3H,d,J=6.8 Hz), 3.716 (3H,s), 4.506(1H,septet,J=6.6 Hz), 5.749(1H,d,J=15.9 Hz), 6.705(1H,dd,J=10.9, 2.2 Hz), 6.735(1H,dt, J=8.3, 8.3, 2.4 Hz), 6.996(1H,dd,J=7.6, 1.5 Hz), 7.041(1H,dd,J=8.3, 6.6 Hz), 7.457(1H,d,J=15.9 Hz), 7.475(1H,dt,J=7.2, 7.2, 1.6 Hz), 7.514(1H,dt,J=7.1, 7.1, 1.7 Hz), 8.450(1H,dd,J=7.3, 2.0 Hz).

Step 5: Methyl
(E)-5-[1,2-dihydro-3-(4-fluoro-2-methoxyphenyl)-2-(1-methylethyl)-1-oxo-4-isoquinolinyl]-3-oxo-4-pentenoate 1,1'-Carbonyldiimidazole (CDI) (393 mg) was added to a solution of the compound (740 mg) obtained by Step 4 in anhydrous tetrahydrofuran (20 ml). The mixture was stirred for 2 hours at room temperature. After addition of magnesium methyl malonate (300 mg), the mixture was stirred at room temperature for 14 hours. The solvent was distilled off, and to the residue was added ethyl acetate. The mixture was washed with aqueous sodium hydrogen carbonate solution and water, dried over anhydrous sodium sulfate and distilled to give the title compound (630 mg) as colorless crystals (keto-enol mixture). mp 164°–166° C. (from ethyl acetate-diethyl ether).

IR$\nu_{max}^{Nujol}$cm$^{-1}$: 1735, 1690, 1640, 1600, 1580, 1320, 1280, 1245.

NMR(200 MHz, CDCl$_3$)ppm: 1.47(3H,d,J=6.8 Hz), 1.59(3H,d,J=6.8 Hz), 3.45 (1.4H,s), 3.72, 3.74(total 3H, each s), 3.79, 3.81(total 3H, each s), 4.03(1H,m), 4.93(0.3H,s), 5.88(0.3H,d,J=16.4 Hz), 6.35(0.6H,d,J=16.4 Hz), 6.73–7.87(6H,m), 8.51(1H,d,J=8 Hz), 11.71(0.3H,s).

Elemental Analysis for C$_{25}$H$_{24}$NO$_5$F: Calculated: C, 68.64; H, 5.52; N, 3.20. Found: C, 68.31; H, 5.50; N, 3.19.

Step 6: Methyl
(E)-5-[1,2-dihydro-3-(4-fluoro-2-methoxyphenyl)-2-(1-methylethyl)-1-oxo-4-isoquinolinyl]-3-hydroxy-4-pentenoate Sodium borohydride (70 mg) was added to a solution of the compound (600 mg) obtained by Step 5 in a mixture of methanol (40 ml) and tetrahydrofuran (20 ml) under ice-cooling. The mixture was stirred for an hour and distilled to remove the solvent. The residue to which ethyl acetate was added was washed with dil. hydrochloric acid and water in turn, dried over anhydrous sodium sulfate and distilled to give the title compound (540 mg) as pale yellow powder.

IR$\nu_{max}^{Neat}$cm$^{-1}$: 3400, 1740, 1630, 1600, 1500, 1405, 1315, 1280.

NMR(200 MHz, CDCl$_3$)ppm: 1.45(3H,d,J=6.8 Hz), 1.59(3H,d,J=6.8 Hz), 2.30(2H, t-like), 3.71(3H,s), 3.80(3H,s), 3.97(1H,m), 4.45(1H,m), 5.55(1H,dd,J=16, 6 Hz), 6.21(1H,d,J=16 Hz), 6.75(2H,m), 7.04(1H,m), 7.45–7.72(3H,m), 8.48(1H,d,J=8 Hz).

EI-MS m/z: 439 (M+).

Step 7:
(E)-5-[1,2-Dihydro-3-(4-fluoro-2-methoxyphenyl)-2-(1-methylethyl)-1-oxo-4-isoquinolinyl]-3-hydroxy-4-pentenoic acid 1N-Sodium hydroxide (3 ml) was added to a solution of the compound (500 mg) obtained by Step 6 in methanol (25 ml) at room temperature under stirring. The mixture was stirred at room temperature for 1.5 hours and then the solvent was distilled off. The residue to which water was added was washed with ethyl acetate. The aqueous layer was acidified with aqueous potassium hydrogen sulfate solution and extracted with ethyl acetate. The extract was washed with water, dried over anhydrous sodium sulfate and distilled to give the title compound (410 mg) as colorless crystals. mp 207°–209° C. (from methanol-diethyl ether).

IR$\nu_{max}^{Nujol}$cm$^{-1}$: 3400, 3100, 1720, 1620, 1600, 1590, 1570, 1280, 1220, 1185.

NMR(200 MHz, CDCl$_3$)ppm: 1.45(3H,d,J=6.6 Hz), 1.59(3H,d,J=6.6 Hz), 2.26(2H, m), 3.80(3H,s), 3.98(1H,m), 4.43(1H,m), 4.74(1H, b), 5.57(1H,dd,J=16.0, 6.4 Hz), 6.19(1H,d,J=16.0 Hz), 6.76(2H,m), 7.05(1H,m), 7.49(1H,m), 7.63 (1H,m), 7.76(1H,m), 8.47(1H,d,J=6.8 Hz).

Elemental Analysis for C$_{24}$H$_{24}$NO$_5$F: Calcualted: C, 67.75; H, 5.69; N, 3.29. Found: C, 67.58; H, 5.58; N, 3.26.

Step 8: Methyl (E)-7-[1,2-dihydro-3-(4-fluoro-2-methoxyphenyl)-2-(1-methylethyl)-1-oxo-4-isoquinolinyl]-5-hydroxy-3-oxo-6-heptenoate 1,1'-Carbonyldiimidazole (170 mg) was added to a soultion of the compound (361 mg) obtained by Step 7 in anhydrous tetrahydrofuran (20 ml), followed by stirring at room temperature for 1.5 hours. The mixture to which magnesium methyl malonate (220 mg) was added was stirred at room temperature for 19 hours. The solvent was distilled off, and to the residue was added ethyl acetate. The mixture was washed with aqueous sodium hydrogen carbonate solution and water in turn, dried over sodium sulfate and distilled to remove the solvent. The resultant residue was subjected to a silica gel column chromatography using ethyl acetate-hexane to give the title compound (160 mg) as pale yellow oily substance.

IR$\nu_{max}^{Neat}$ cm$^{-1}$: 3400, 1745, 1571, 1630, 1500, 1445, 1405, 1330, 1280.

NMR(200 MHz, CDCl$_3$)ppm: 1.45(3H,d,J=6.8 Hz), 1.59(3H,d,J=6.6 Hz), 2.51(2H, m), 3.45(2H,s), 3.76(3H,s), 3.80(3H,d,J=1.4 Hz), 3.97(1H,m), 4.51(1H,m), 5.52(1H,dd,J=1.6, 6.6 Hz), 6.21(1H,d,J=16 Hz), 6.76(2H,m), 7.04(1H,m), 7.45–7.70(3H,m), 8.48(1H,d,J=8.2 Hz).

EI-MS m/z: 481 (M+).

REFERENCE EXAMPLE 2

Methyl (E)-7-[1,2-dihydro-2-(4-fluorophenyl)-2-(1-methylethyl)-1-oxo-4-isoquinolinyl]-5-hydroxy-3-oxo-heptenoate Step 1: Ethyl 4-{N-[2-(4-fluorobenzoyl)benzyol]-N-isopropylamino} crotonate Thionyl chloride (1.6 ml) was added to a solution of 2-(4-fluorobenzoyl)benzoic acid (3.6 g) and pyridine (0.03 ml) in benzene (40 ml), followed by refluxing for an hour. The solvent was distilled off to give 2-(4-fluorobenzoyl) benzoyl chloride (IR$\nu_{max}^{Nujol}$: 1790 cm$^{-1}$).

A solution of this product in methylene chloride (40 ml) was added to a solution of ethyl 4-isopropylamino crotonate (Reference Example 1) (3.9 g) and triethylamine (3.0 ml) in methylene chloride (40 ml), followed by stirring at room temperature for 16 hours. After removing the solvent, the residue to which ethyl acetate was added was washed with water, dil. hydrochloric acid, water, aqueous sodium hydrogen carbonate solution and water in turn. The ethyl acetate layer was dried over anhydrous sodium sulfate and distilled to give the title compound (4.59 g) as colorless crystals. mp 106°–170° C. (from ethyl acetate-n-hexane).

IR$\nu_{max}^{Nujol}$ cm$^{-1}$: 1725, 1660, 1620, 1595, 1270, 1225, 1170.

NMR(90 MHz, CDCl$_3$)ppm: 1.20(6H,d,J=7 Hz), 1.27(3H,t,J=7 Hz), 4.05(3H,bm), 4.18(2H,q,J=7 Hz), 5.93(1H,d,J=16 Hz), 6.86(1H,dt, J=16, 6 Hz), 7.00–7.95(8H,m).

Elemental Analysis for C$_{23}$H$_{24}$NO$_4$F: Calculated: C, 69.51; H, 6.09; N, 3.52. Found: C, 69.71; H, 6.11; N, 3.56.

Step 2: Ethyl (E)-3-[4-(4-fluorophenyl)-4-hydroxy-2-(1-methylethyl)-1-oxo-1,2,3,4-tetrahydro-3-isoquinolinyl]-2-propenoate 1,8-Diazabicyclo[5.4.0]undec-7-ene (1.7 ml) was added to a suspension of the compound (1.71 g) obtained by Step 1 in anhydrous toluene (75 ml), followed by refluxing for an hour under stirring. After removing the solvent, the residue to which ethyl acetate was added was washed with aqueous potassium hydrogen sulfate solution and water. The ethyl acetate layer was dried over anhydrous sodium sulfate and distilled to remove the solvent, thereby affording the title compound (1.42 g) as colorless crystals. mp 220°–221° C. (from acetone-isopropyl ether).

IR$\nu_{max}^{Nujol}$ cm$^{-1}$: 3350, 1715, 1620, 1600, 1265.

NMR(200 MHz, CDCl$_3$)ppm: 0.41(3H,d,J=7 Hz), 0.99(3H,d,J=7 Hz), 1.29(3H,t, J=7 Hz), 2.71(1H,s), 4.08–4.22(3H,m), 4.78(1H,m), 6.08(1H,d,J=16 Hz), 6.77–7.60(8H,m), 8.18(1H,m).

Elemental Analysis for C$_{23}$H$_{24}$NO$_4$F: Calculated: C, 69.51; H, 6.09; N, 3.52. Found: C, 69.53; H, 6.16; N, 3.46.

Step 3: Ethyl (E)-3-[1,2-dihydro-3-(4-fluorophenyl)-2-(1-methylethyl)-1-oxo-4-isoquinolinyl]-2-propenoate The compound obtained in Step 2 was reacted and treated in the same way as in Step 3 of Reference Example 1 to give a mixture of the title compound and its position isomer i.e., ethyl (E)-3-[1,2-dihydro-4-(4-fluorophenyl)-2-(1-methylethyl)-1-oxo-3-isoquinolinyl]-2-propenoate (about 4:3 by NMR spectrum). This mixture was treated with isopropyl ether to give the title compound as colorless crystals. Further the mother liquir was subjected to a silica gel column chromatography, eluting with benzene-ethyl acetate, to give the title compound and its position isomer each as colorless crystals.

Physicochemical data of the title compound:

mp 167°–169° C. (from isopropyl ether-diethyl ether).

IR$\nu_{max}^{Nujol}$ cm$^{-1}$: 1705, 1655, 1630, 1600, 1330, 1300, 1250, 1210, 1180.

NMR(200 MHz, CDCl$_3$)ppm: 1.25(3H,t,J=7 Hz), 1.53(6H,d,J=7 Hz), 4.04(1H,m), 4.16(2H,q,J=7 Hz), 5.97(1H,d,J=16 Hz), 7.10–7.40 (5H,m), 7.55(1H,t,J=7 Hz), 7.69 (1H,t,J=7 Hz), 7.90 (1H,d,J=8 Hz), 8.51(1H,d,J=8 Hz).

Elemental Analysis for C$_{23}$H$_{22}$NO$_3$F: Calculated: C, 72.81; H, 5.84; N, 3.69. Found: C, 73.05; H, 5.92; N, 3.68.

Physicochemical data of the position isomer:

mp 110°–111° C. (from ethyl acetate-n-hexane).

IR$\nu_{max}^{Nujol}$ cm$^{-1}$: 1720, 1645, 1600, 1320, 1275, 1220, 1170.

NMR(200 MHz, CDCl$_3$)ppm: 1.25(3H,t,J=7 Hz), 1.69(6H,d,J=7 Hz), 4.16(2H,q,J=7 Hz), 4.52(1H,m), 5.69(1H,d,J=16 Hz), 7.02–7.54 (8H,m), 8.47(1H,m).

Elemental Analysis for C$_{23}$H$_{22}$NO$_3$F: Calculated: C, 72.81; H, 5.84; N, 3.69. Found: C, 72.65; H, 5.91; N, 3.69.

Further, the title compound of Step 3 was treated in the same way as in Steps 4–8 of Reference Example 1 to give the title compound of Reference Example 2. Physicochemical data of the compound obtained by each Steps are as follows.

Step 4: (E)-3-[1,2-dihydro-3-(4-fluorophenyl)-2-(1-methylethyl)-1-oxo-4-isoquinolinyl]-2-propenoic acid mp 233°–234° C. (from ethyl acetate).

IR$\nu_{max}^{Nujol}$ cm$^{-1}$: 3100, 1720, 1640-1600, 1505, 1330, 1290, 1255, 1220, 1170.

NMR(200 MHz, CDCl$_3$)ppm: 1.53(6H,d,J=7 Hz), 4.04(1H,m), 5.96(1H,d,J=16 Hz), 7.10-7.28(5H,m), 7.56(1H,dt,J=7,1 Hz), 7.71(1H, dt,J=7,1 Hz), 7.90(1H,d,J=7 Hz), 8.51(1H,dt,8, 1 Hz).

Step 5: Methyl (E)-5-[1,2-dihydro-3-(4-fluorophenyl)-2-(1-methylethyl)-1-oxo-4-isoquinolinyl]-3-oxo-4-pentenoate [keto-enol mixture]

mp 123°-125° C. (from isopropyl ether).
IR$\nu_{max}^{Nujol}$ cm$^{-1}$: 1645, 1630, 1600, 1240, 1220, 1150.
NMR(200 MHz, CDCl$_3$)ppm: 1.53(6H,d,J=7 Hz), 3.44(1H,s), 3.63, 4.94(each ca.0.25H, each s), 3.72, 3.74, 3.76(total 3H, each s), 4.04(1H,m), 5.87, 5.97(each ca.0.25H, each d,J=16 Hz), 6.36(each ca.0.5H,d,J=16 Hz), 6.91-7.33(5H,m), 7.52-7.93(3H,m), 8.51(1H,dd,J=8, 1.4 Hz).

Step 6: Methyl (E)-5-[1,2-dihydro-3-(4-fluorophenyl)-2-(1-methylethyl)-1-oxo-4-isoquinolinyl]-3-hydroxy-4-pentenoate mp 167°-168° C. (from ethyl acetate-isopropyl ether)
IR$\nu_{max}^{Nujol}$ cm$^{-1}$: 3450, 1730-1700, 1640, 1600, 1510, 1325, 1275, 1220, 1170, 1100.
NMR(200 MHz, CDCl$_3$)ppm: 1.53(6H,d,J=7 Hz), 2.31(2H,m), 3.45(1H,s), 3.71(3H,s), 4.03(1H,m), 4.47(1H,m), 5.53(1H,dd,J=16, 6 Hz), 6.18(1H,dd,J=16, 2 Hz), 7.11-7.24 (4H,m), 7.45-7.80(3H,m), 8.49(1H,dd,J=8, 1 Hz)

Step 7: (E)-5-[1,2-Dihydro-3-(4-fluorophenyl)-2-(1-methylethyl)-1-oxo-4-isoquinolinyl]-3-hydroxy-4-pentenoic acid mp 225°-227° C. (from acetone-ethyl acetate)

IR$\nu_{max}^{Nujol}$ cm$^{-1}$: 3380, 3100, 1715, 1625, 1600, 1580, 1510, 1330, 1235, 1155.
NMR(200 MHz, CDCl$_3$)ppm: 1.52(6H,d,J=7 Hz), 2.29(2H,m), 4.04(1H,m), 4.43(1H,m), 5.56(1H,dd,J=16, 6 Hz), 6.15(1H,dd,J=16, 1 Hz), 7.2(4H,m), 7.50(1H,t-like,J=7 Hz), 7.65(1H, t-like,J=7 Hz), 7.80(1H,d,J=8 Hz), 8.47(1H,dd,J=8, 2 Hz)

Step 8: Methyl (E)-7-[1,2-dihydro-3-(4-fluorophenyl)-2-(1-methylethyl)-1-oxo-4-isoquinolinyl]-5-hydroxy-3-oxo-6-heptenoate mp 147°-149° C. (from ethyl acetate-isopropyl ether).
IR$\nu_{max}^{Nujol}$ cm$^{-1}$: 3400, 1740, 1715, 1645, 1605, 1510, 1220.
NMR(200 MHz, CDCl$_3$)ppm: 1.53(6H,d,J=7 Hz), 2.54(2H,m), 3.45(2H,s), 3.76(3H,s), 4.04(1H,m), 4.50(1H,m), 5.50(1H,dd,J=16, 6 Hz), 6.17(1H,dd,J=16, 1.4 Hz), 7.13-7.75 (7H,m), 8.49(1H,d,J=8 Hz).

REFERENCE EXAMPLES 3-12, 45-48 (REACTION SCHEME 4, TABLE 3)

Compounds 3I-12I were obtained from substituted benzoylbenzoic acids (Compound A) and N-substituted aminocrotonic esters (Reference Examples I and II) as the starting materials by treating in the same way as in Steps 1-8 of Reference Examples 1 and 2 (Reaction Scheme 4).

As far Compounds 45 and 46, compounds 45D and 46D were prepared in accordance with the method as in Steps 1-3 of Reference Example IV and converted into Compounds 45I and 46I, respectively. The production of Compounds 45D and 46D will be stated later.

With respect to Compounds 47 and 48, Compounds 47I and 48I were prepared by using 1-(2-substituted benzoyl) cyclohexenecarboxylic acid instead of the substituted benzoylbenzoic acid of Reference Examples 1-2 in accordance with Steps of Reaction Scheme 4.

Also, in the production of Compounds 46I-48I, Compounds 46G-48G was converted into Compounds 46H-48H, which was without isolation, reacted with anion of t-butyl acetate to isolate t-butyl ester of Compounds 46I-48I.

Some physicochemical properties of Compounds obtained by each Steps are shown in Table 3. In the Table, the ring A for Compounds 3-12, 45 and 46 means

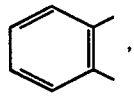, and the ring A for Compounds 47 and 48 means

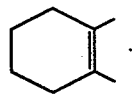.

Reaction Scheme 4

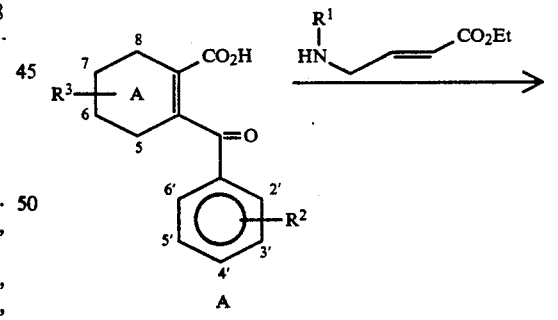

A

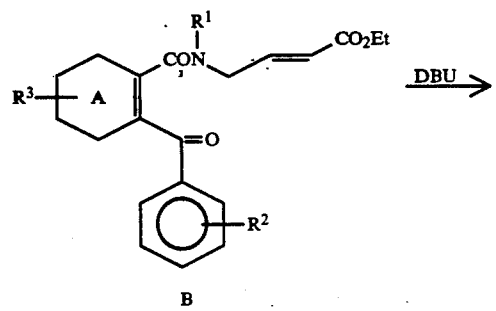

B

-continued
Reaction Scheme 4
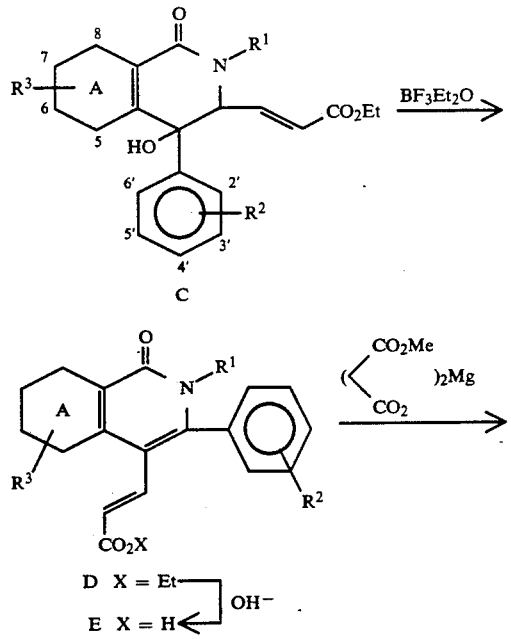
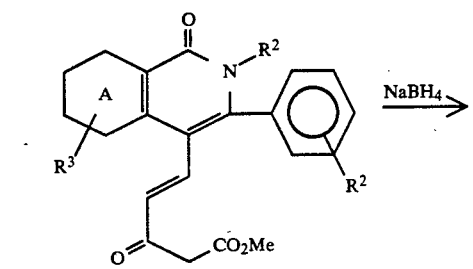
-continued
Reaction Scheme 4
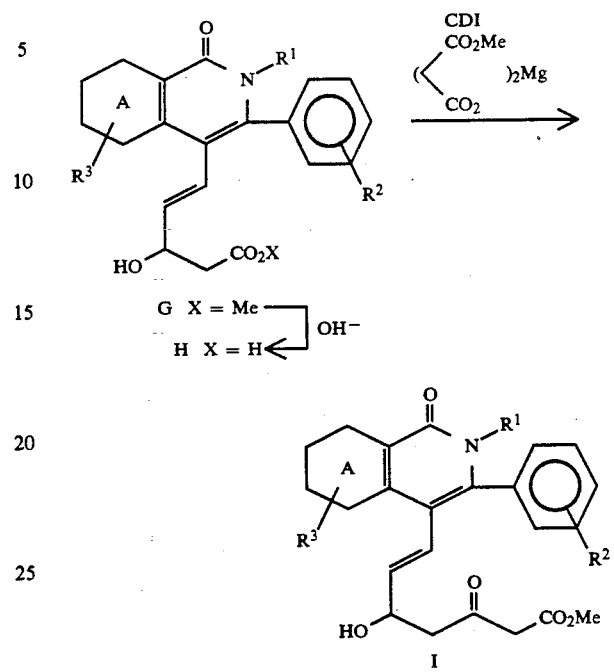
TABLE 3
| Ref. Ex. (Comp) No. | R¹ | R² | R³ | A | B | C |
|---|---|---|---|---|---|---|
| 3 | —CHMe₂ | 2'-F, 4'-MeO | H | 158–159 | 65–66 | 176–177 |
| 4 | " | 2'-MeO, 5'-F | " | 142–143 | (*) | 182–183 |
| 5 | " | 2'-Me, 4'-F | " | 130–131 | 112–113 | 208–209 |
| 6 | " | 2'-F, 4'-F | " | 137–138 | 105–106 | 188–190 |
| 7 | " | 4'-F | 6-Me | 179–181 | 108–110 | 219–220 |
| 8 | " | " | 6-Me, 7-Me | 202–203 | 115–116 | 190–191 |
| 9 | " | " | 6-F | 169–170 | (*) | 213–215 |
| 10 | —(CH₂)₂Me | 2'-Me, 4'-F | H | R.E. 5-A ¹ | (*) | 190–191 |
| 11 | " | 2'-F, 4'-F | " | R.E. 6-A ¹ | (*) | 133–134 |
| 12 | " | 4'-F 4'-F | 8-Me | 153–155 | (*) | 172–173 |
| 45 | —(CH₂)₂—F | 4'-F | H | — | — | — |
| 46 | —(CH₂)₂—C(=O)NMe₂ | " | " | — | — | — |
| 47 (*⁴) | " | " | " | 125–126 | oily | 182–184 |
| 48 (*⁴) | " | " | " | R.E. 47-A ¹ | (*) | 144–145 |
| Ref. Ex. (Comp) No. | D | E | F | G | H | I |
|---|---|---|---|---|---|---|
| 3 | 101–103 | 253–255 | 128–130 | 113–115 | 233–235 | oily |
| 4 | (*) | 252–255 | 129–131 | oily | 200–202 | 71–72 (hydrate) |
| 5 | 158–159 | 206–208 | 134–136 | 145–146 | 211–213 | 134–135 |
| 6 | 154–156 | 252–254 | 119–121 | 152–154 | 241–242 | 129–131 |
| 7 | 202–204 | 230–231 | 123–125 | 134–135 | 239–240 | 142–141 |
| 8 | 191–192 | 230–232 | 161–163 | 145–146 | 206–208 | 123–125 |
| 9 | (*) | 222–224 | 141–143 | 155–157 | 236–238 | 148–149 |
| 10 | (*) | 203–205 | oily | oily | 171–173 | oily |

TABLE 3-continued

| 11 | (*) | 220–222 | oily | 113–115 | 156–158 | oily |
| 12 | (*) | 221–223 | oily | oily | 188–189 | 109–110 |
| 45 | 136–137 (*1) | 192–195 | oily | oily | 140–142 | oily |
| 46 (*4) | 96–98 (*2) | 219–222 | 70–73 | 160–163 | — | oily (*3) |
| 47 (*4) | 127–128 | 259–261 | 170–172 | 113–115 | — | 128–129 (*3) |
| 48 (*4) | oily | 244–245 | oily | 87–89 | — | 117–119 (*3) |

(*) means to use without isolation in subsequent step
(*1) means to prepare from 2-(2-fluoroethyl)-3-(4-fluorophenyl)-1-(2H)-isoquinoline (Reference Example 45)
(*2) means to prepare from 2-(2-ethoxycarbonylethyl)-3-(4-fluorophenyl)-1-(2H)-isoquinoline (Reference Example 46)
(*3) compound I(t-butyl ester) was obtained by reacting Compound G with t-butyl acetate anion (*4) The ring A for Compounds 47 and 48 is 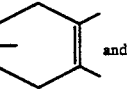 and the ring A for other compounds means 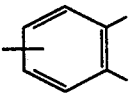

The data (ppm) of 200 MHz NMR spectra (in CDCl$_3$) of the compounds obtained as oily substance in Table 3 were shown as follows:

3 I: 1.51(3H,d,J=7 Hz),1.59(1H,d,J=7 Hz), 2.42-2.62(3H,m),3.45(3H,m),3.75(3H,s),3.89 (3H,s),4.08(1H,m),4.45-4.62(1H,m),5.50-5.67(1H,m),6.- 17-6.34(1H,m),6.69-6.88(2H,m), 7.09(1H,dt,J=8,2 Hz),7.45-7.76(3H,m),8.49(1H,d,J=8 Hz).

4 G: 1.48(3H,d,J=7 Hz),1.60(3H,d,J=7 Hz), 2.21-2.35(2H,m),2.56-2.80(1H,m),3.71(3H,s), 3.79(3H,s);3.97(1H,m),4.41-4.54(1H,m),5.- 48-5.65(1H,m),6.25(1H,d,J=16 Hz),6.80-6.97(2H, m),7.07-7.22(1H,m),7.45-7.74(3H,m),8.49(1H, d,J=7 Hz).

10 F: 0.74(3H,t,J=7 Hz),1.45(1H,m),1.66(1H, m),2.10(3H,s),3.28(1H,m),3.44(1.2H,s),3.71, 3.74(total 3H,each s),4.10(1H,m),4.93(0.4H, s),5.86(0.4H,d,J=16 Hz),6.35(0.6H,d,J=16 Hz), 6.96-7.26(4H,m),7.- 52-7.95(3H,m),8.55(1H,d, J=7 Hz),11.7(0.4H,b).

10 G: 0.73(3H,t,J=7 Hz),1.3-1.8(2H,m),2.09(3H,s),2.32(2H,m),2.8(1H,m),3.- 15-3.35(1H, m),3.71(3H,s),4.11(1H,m),4.47(1H,m),5.56(1H,dd,J=1- 6,6 Hz),6.21(1H,d,J=16 Hz),7.01-7.21(3H,m),7.- 50-7.83(3H,m),8.53(1H,d,J=8 Hz).

10 I: 0.73(3H,t,J=7 Hz),1.35-1.75(2H,m), 2.10(3H,s),2.50(2H,m),2.61(1H,m),3.2-3.3(1H,m),3.44(- 2H,s),3.75(3H,s),4.05-4.20(1H,m), 4.53(1H,m),5.51(1H,dd,J=16,6 Hz),6.17(1H,d, J=16 Hz),6.57-7.21(3H,m),7.49-7.81(3H,m), 8.52(1H,d,J=8 Hz).

11 F: 0.76(3H,t,J=7 Hz),1.47-1.64(2H,m), 3.49(0.8H,s),3.6-3.7(1H,m), 3.73,3.74(total 3H,each s),3.8-4.0(1H,m),4.96(0.6H,s),5.89(0.6H,dd,J=16,1 Hz),6.37(0.4H,d,J=16 Hz), 6.98-7.31(4H,m),7.- 53-7.89(3H,m),8.54(1H,d, J=8 Hz),11.71(0.6H,s).

11 I: 0.75(3H,t,J=7 Hz),1.39-1.72(2H,m), 2.48-2.69(3H,m),3.45(2H,s),3.54-3.76(1H,m), 3.76(3H,s),3.80-3.98(1H,m),4.47-4.65(1H,m), 5.48-5.64(1H,m),6.23-6.38(1H,m),6.89-7.10(2H,m),7.- 15-7.36(1H,m),7.48-7.81(3H,m),8.53(1H,dd,J=8,1 Hz).

12 F: 0.73(3H,t,J=7 Hz),1.50-1.62(2H,m), 2.98(3H,s),3.42(1.2H,s),3.64-3.76(2H,m), 3.72,3.73(total 3H,each s),4.90(0.4H,s), 5.77(0.4H,d,J=16 Hz),6.27(0.6H,d,J=16 Hz), 7.01-7.40(6H,m),7.- 50-7.58(1H,m),7.68-7.75(1H,m),11.7(0.4H,b).

12 G: 0.72(3H,t,J=7 Hz),1.3(1H,m),1.5-1.6(2H,m),2.26(2H,m),2.98(3H,s),3.- 70(3H,s),3.64-3.72(2H,m),4.45(1H,m),5.43(1H,dd,J=1- 6,6 Hz),6.25(1H,dd,J=16,1 Hz),7.10-7.59(7H,m).

45 F: 3.45(1.2H,s),3.72,3.74(3H,each s), 4.15(2H,dt,J=24,4.9 Hz),4.65(2H,dt,J=47,4.9 Hz),4.94(0.4H,s),5.86(0.4H,dd,J=16,1 Hz), 6.36(0.6H,d,J=16 Hz),7.03(0.4H,d,J=16 Hz), 7.15-7.35(4.6H,m),7.50-7.80(2H,m),7.- 85-7.95(1H,m),8.54(1H,d,J=7.6 Hz).

45 G: 2.31(2H,d like,J=6.0 Hz),2.88(1H,bs), 3.70(3H,s),4.14(2H,dt,J=24,4.9 Hz),4.47(1H, m),4.64(2H,dt,J=48,4.9 Hz),5.55(1H,dd,J=10, 6.0 Hz),6.25(1H,dd,J=16,1.4 Hz),7.10-7.35(4H, m),7.50-7.85(3H,m),8.51(1H,d,J=8.0 Hz).

45 I: 2.51(2H,d like,J=6.0 Hz),2.64(1H,d,J=4.0 Hz),3.44(2H,s),3.75(3H,s),4.14(2H,dt,J=24,4.9 Hz),4.55(1H,b),4.65(2H,dt,J=47,4.9 Hz),5.52(1H,dd,J=16,6.0 Hz),6.24(1H,dd,J=16, 1.4 Hz),7.10-7.35(4H,m),7.50-7.85(3H,m), 8.51(1H,dd,J=7.0,0.8 Hz).

46 I (t-butylester): 1.47(9H,s),2.49(2H,d,J=5.6 Hz),2.64(2H,t like,J=8.0 Hz),2.82(1H,d,J=4.2 Hz),2.85(3H,s),2.97(3H,s),3.33(2H, s),4.10(2H,t li- ke,J=8.0 Hz),4.52(1H,bm), 5.51(1H,dd,J=16,5.8 Hz),6.22(1H,dd,J=16,1.4 Hz),7.10-7.30(4H,m),7.- 45-7.85(3H,m),8.49(1H,dd,J=8.2,1.4 Hz).

47 B: 1.13(6H,d,J=7 Hz),1.26(3H,t,J=7 Hz), 1.60-1.94(4H,m),2.17-2.50(4H,m),3.78(2H,d, J=5 Hz),4.00-4.32(3H,m),5.61(1H,d,J=16 Hz), 6.28-6.50(1H,m),7.00-7.18(2H,m),7.82-8.03(2H,m).

48 D: 0.71(3H,t,J=7.4 Hz),1.21(3H,t,J=7 Hz), 1.55(2H,m),1.7-1.8(4H,m),2.6(4H,bs),3.67(2H,m),4.10(- 2H,q,J=7 Hz),5.54(1H,d,J=16 Hz), 7.1-7.2(4H,m).

48 F: 0.71(3H,t,J=7 Hz),1.42-1.91(6H,m), 2.50-2.75(4H,m),3.34(1.2H,s),3.59-3.80(2H, m),3.69(1.8H,s),3.71(1.2H,s),4.79(0.4H,s), 5.41(0.4H,dd,J=16,1 Hz),5.90(0.6H,d,J=16 Hz), 6.88(0.4H,d,J=16 Hz),7.08(0.6H,d,J=16 Hz), 7.14-7.37(4H,m).

REFERENCE EXAMPLE 13

Step 1:

3-(4-Fluorophenyl)-2-(1-phenylethyl)-1-(2H)-isoquinoline

β-Phenethylamine (5 ml) was added to a solution of the compound (1.50 g) obtained by Reference Example III-1 in ethanol, followed by refluxing for 6 hours. After cooling, the reaction mixture to which ethyl acetate was added was washed with water, 1N hydrochloric acid and water in turn, dried over magnesium sulfate and then distilled to remove the solvent. The residue was dissolved in a solution of 4N-hydrochloric acid in ethyl acetate (20 ml), followed by stirring at room temperature for 1 hour. The mixture to which water was added was extracted with ethyl acetate. The extract was washed with water and dried over magnesium sulfate and the solvent was distilled off to give the title compound (2.07 g) as colorless crystals.

mp 85°–87° C. (from diethyl ether).

$IR\nu_{max}^{Nujol}cm^{-1}$: 1740, 1640, 1615, 1590, 1505, 1330, 1215.

NMR(200 MHz, CDCl$_3$)ppm: 2.89(2H,t,J=8.0 Hz), 4.14(2H,t,8.0 Hz), 6/37(1H,s), 6.80–7.00(2H,m), 7.05–7.40(7H,m) 7.40–7.75(3H,m), 8.49(1H, d,J=8.0 Hz).

Elemental Analysis for $C_{23}H_{18}NOF$: Calculated: C, 80.45; H, 5.28; N, 4.08. Found: C, 80.39; H, 5.74; N, 3.95.

REFERENCE EXAMPLE 13

Step 2:
(E)-3-[1,2-Dihydro-3-(4-fluorophenyl)-2-(2-phenylethyl)-1-oxo-4-isoquinolinyl]prop-2-enal In an atmosphere of nitrogen gas, a solution of 3-N,N-dimethylaminoacrolein (3.7 ml) in anhydrous acetonitrile (10 ml) was added to a solution of phosphorous oxychloride (3.7 ml) in anhydrous acetonitrile (15 ml) at −10° C. under stirring and taking 15 minutes. To this solution was added the compound (1.8 g) obtained in Step 1 of Reference Example 13. The mixture was refluxed for 36 hours. After cooling, the reaction mixture was added slowly to an aqueous solution (50 ml) of sodium hydroxide (7.8 g) which was cooled at 0° C. Further the mixture to which chloroform was added was stirred slowly at room temperature and filtered through celite to remove an insoluble substance. The extract was washed, dried over magnesium sulfate and distilled to remove the solvent. The residue was subjected to a silica gel column chromatography, eluting with ethyl acetate-n-hexance to give the title compound (835 mg) as colorless crystals. mp 133°–134° C.

$IR\nu_{max}^{Nujol}cm^{-1}$: 1670, 1630, 1615, 1590, 1310, 1220, 1120.

NMR(200 MHz, CDCl$_3$)ppm: 2.89(2H,t,J=8.0 Hz), 4.01(2H,t,8.0 Hz), 6:35(1H,dd, J=16, 7.6 Hz), 6.80–6.95(2H,m), 7.02(1H,d,J=16 Hz), 7.05–7.30(7H,m), 7.55–7.85(2H,m), 7.93(1H,d, J=8.4 Hz), 8.55–8.65(1H,m), 9.36(1H,d,J=7.6 Hz).

Elemental Analysis for $C_{26}H_{20}NO_2F$: Calculated: C, 78.57; H, 5.97; N, 3.52. Found: C, 78.98; H, 4.97; N, 3.56.

REFERENCE EXAMPLE 13

Step 3: Methyl (E)-7-[1,2-dihydro-3-(4-fluorophenyl)-2-(2-phenylethyl)-1-oxo-4-isoquinolinyl]-5-hydroxy-3-oxo-6-heptenoate In an atmosphere of argon gas, methyl acetoacetate (0.29 ml) was added to a suspension of sodium hydride (60%, in oil) (129 mg) in anhydrous tetrahydrofuran (15 ml) at 0° C. under stirring, followed by stirring for 10 minutes. After cooling at −78° C., the mixture to which a solution of n-butyllithium in n-hexane (1.6M, 2.7 ml) was added was stirred for 10 minutes. A solution of the compound (748 mg) obtained by Step 2 of Reference Example 13 in anhydrous tetrahydrofuran (7 ml) was added to the mixture, followed by stirring at −78° C. for 30 minutes. The reaction mixture to which aqueous ammonium chloride solution was added was extracted with ethyl acetate. The extract was washed with water, dried over anhydrous magnesium sulfate and distilled to remove the solvent. The residue was subjected to a silica gel column chromatography using ethyl acetate-n-hexane to give the title compound (768 mg) as pale yellow oily substance.

$IR\nu_{max}^{Neat}cm^{-1}$: 3400, 1750, 1710, 1660, 1630, 1595, 1570, 1480, 1320, 1220.

NMR(200 MHz, CDCl$_3$)ppm: 2.51(2H,d-like,J=6 Hz), 2.60(1H,d,J=4 Hz), 2.87(2H,d-like,J=8 Hz), 3.45(2H,s), 3.76(3H,s), 4.01(2H,t-like,J=8 Hz), 4.54(1H,b), 5.50(1H,dd, J=16,5.8 Hz), 6.24(1H,dd,J=16,1.4 Hz), 6.85–7.00 (2H,m), 7.05–7.35(7H,m), 7.50–7.85(3H,m), 8.57(1H,dd,J=7,0.8 Hz).

EI-MS m/z: 513(M+).

REFERENCE EXAMPLES 14–44

The compounds 14 I–44 I were obtained from the compounds J-1-J-6 and substituted amines as starting materials by treating in accordance with the method as in Steps 1–3 of Reference Example 13 (Reaction Scheme 5). Some physicochemical properties of the compound obtained by each step are shown in Table 4.

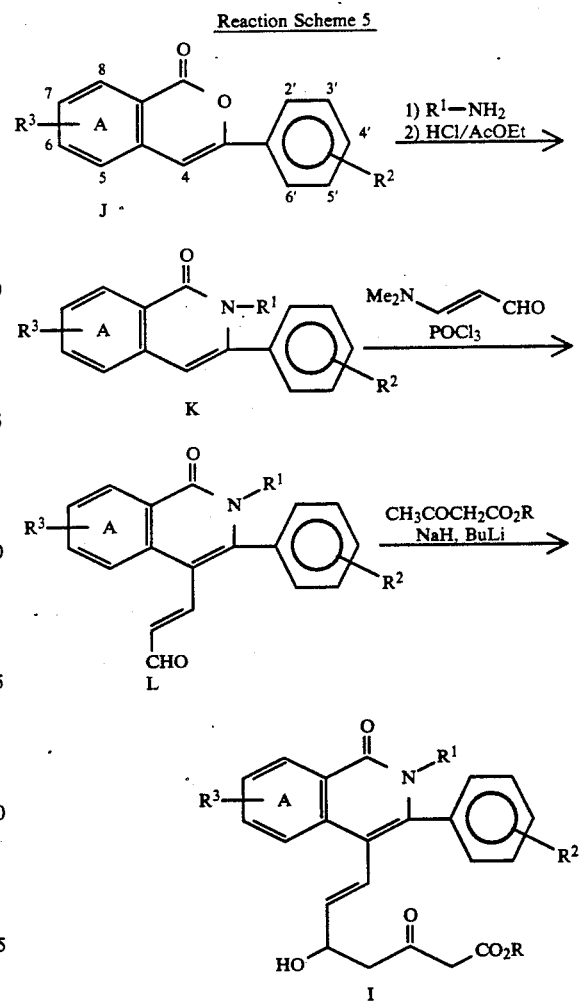

Reaction Scheme 5

TABLE 4

| Reference Example No. | R¹ | R² | R³ | K | L | I*¹ |
|---|---|---|---|---|---|---|
| 14 | Me | 4'-F | H | 138-140 | 196-198 | 94-97 |
| 15 | Et | " | " | 130 | 175 | 90 |
| 16 | —(CH₂)₂Me | " | " | 85-86 | 177-179 | 87-89 |
| 17 | —(CH₂)₃Me | " | " | 115-116 | 169-170 | oily |
| 18 | —(CH₂)₄Me | " | " | 96 | 119-112 | oily |
| 19 | —(CH₂)₆Me | " | " | 81-82 | 111-113 | 70-71 |
| 20 | —(CH₂)₃Me | " | " | 65 | 74-76 | 85-88 |
| 21 | —CH₂CHMe₂ | " | " | 104 | 142-143 | oily |
| 22 | —cyclopropyl | " | " | 174-175 | 157-160 | oily |
| 23 | —cyclohexyl | " | " | 154-155 | 210-212 | 154-155 |
| 24 | —CH₂Ph | " | " | 142-144*² | 114 | oily |
| 25 | —(4-F-C₆H₄) | " | " | 240-242 | 208-210 | 150-151 |
| 26 | —CHMe₂ | " | 5-Me | 172-173 | 184 | 135-138 |
| 27 | —(CH₂)₂Me | " | " | 102-103 | 119-121 | 93-96 |
| 28 | " | " | 5-F | 104 | oily | oily |
| 29 | " | " | 5-Cl | 117-118 | oily | oily |
| 30 | —(CH₂)₂Me | 4'-F | 5-MeO | 64-66 | oily | oily |
| 31 | —CHMe₂ | 4'-Me | H | 163-164 | 181-183 | 127 |
| 32 | —(CH₂)₃Ph | 4'-F | " | 95 | 144 | 100 |
| 33 | —(CH₂)₂(4-Cl-C₆H₄) | " | " | 136-137 | 151-154 | oily |
| 34 | —(CH₂)₃Ph | 4'-F | H | 95 | 144 | 100 |
| 35 | —(CH₂)₃Ph | " | " | 136-138 | 150-153 | oily |
| 36 | —(CH₂)₃(4-Me-C₆H₄) | " | " | 171-174 | 163-166 | oily |
| 37 | —(CH₂)₂(4-OMe-C₆H₄) | " | " | 141-143 | 160-161 | oily |

TABLE 4-continued

| Reference Example No. | R¹ | R² | R³ | K | L | I*¹ |
|---|---|---|---|---|---|---|
| 38 | MeO−(CH₂)₂−C₆H₄− | " | " | 103–105 | 186–189 | oily |
| 39 | F−(CH₂)₂−C₆H₄− (para-F) | " | " | 129–131 | 165–167 | oily |
| 40 | F−(CH₂)₂−C₆H₄− (ortho-F) | " | " | 130–132 | 143–145 | oily |
| 41 | −(CH₂)₂−OMe | " | " | 104–106 | oily | oily |
| 42 | −(CH₂)₂−SMe | " | " | 124 | oily | oily |
| 43 | −CH₂−CH=CH₂ | " | " | 105–106 | 127–130 | oily |
| 44 | −(CH₂)₂−C₆H₄−CF₃ | " | " | 127–130 | 111–114 | 115–118 |

*¹Compounds 14I, 16I, 22I and 31I are ethyl esters and the others are methyl ester.
*²The value in the literature: mp 142–143° C. [A. Couture and P. Grandclaudon, Synthesis, 576(1986)]

The data (ppm) of 200 MHZ NMR spectra (in CDCl₃) of the compounds obtained as oily substances in Table 4 are as follows.

1 7 I: 0.74(3H,t,J=7 Hz), 1.05–1.25(2H,m), 1.45–1.65(2H,m), 2.52(2H,m), 2.60(1H,d,J=4 Hz), 3.44(2H,s), 3.75(3H,s), 3.75–3.85(2H,m), 4.53(1H,b), 5.50(1H,dd,J=16,6 Hz), 6.23(1H,dd, J=16,1 Hz), 7.10–7.30(4H,m), 7.45–7.80(3H,m), 8.51(1H,dd,J=8,1 Hz).

1 8 I: 0.79(3H,t,J=7 Hz), 1.00–1.30(4H,m), 1.45–1.65(2H,m), 2.45–2.60(3H,m), 3.45(2H,s), 3.70–3.85(2H,m), 3.76(3H,s), 4.53 (1H,b), 5.51 (1H,dd,J=16,6 Hz), 6.24(1H,dd,J=16,1 Hz), 7.10–7.35(4H,m), 7.45–7.85(3H,m), 8.52(1H,d,J=7 Hz).

2 1 I: 0.73(6H,d,J=7 Hz), 1.92(1H,m), 2.53(2H, m), 2.62(1H,d,J=4 Hz), 3.45(2H,s), 3.65–3.90(2H, m), 3.76(3H,s), 4.54(1H,b), 5.49(1H,dd,J=16, 6 Hz), 6.24(1H,dd,J=16,1 Hz), 7.10–7.35(4H,m), 7.45–7.85(3H,m), 8.52(1H,d,J=8 Hz).

2 2 I: 0.50–0.65(2H,m), 0.75–0.85(2H,m), 1.28(3H,t,J=7 Hz), 2.58(2H,d,5 Hz), 2.70–2.85(2H,m), 3.44(2H,s), 4.21(2H,q,J=7 Hz), 4.58(1H, b), 5.49(1H,dd,J=16,6 Hz), 6.34(1H,dd,J=16,1 Hz), 7.05–7.35(4H,m), 7.45–7.80(3H,m), 8.47(1H,dd,J=7,8,1 Hz).

2 4 I: 2.40–2.55(2H,m), 2.57(1H,d,J=4 Hz), 3.42(2H,s), 3.74(3H,s), 4.51(1H,b), 5.16(2H, s), 5.49(1H,dd,J=16,6 Hz), 6.23(1H,dd,J=16,1 Hz), 6.75–7.25(9H,m), 7.50–7.85(3H,m), 8.59(1H,dd,J=8,1 Hz).

2 8 L: 0.73(3H,t,J=7 Hz), 1.45–1.65(2H,m), 3.65–3.80(2H,m), 5.72(1H,ddd,J=16,8 Hz), 7.15–7.60(7H,m), 8.37(1H,dd,J=8,1 Hz), 9.37(1H,d, J=8 Hz).

2 8 I: 0.72(3H,t,J=7 Hz), 1.45–1.70(2H,m), 2.34(1H,d,J=4 Hz), 2.35(2H,m), 3.43(2H,s), 3.65–3.80(2H,m), 3.75(3H,s), 4.45(1H,b), 5.20(1H,dd,J=16,7 Hz), 6.47(1H,ddd,J=16,9,1 Hz), 7.10–7.50(6H,m), 8.34(1H,dd,J=8,1 Hz).

2 9 L: 0.73(3H,t,J=7 Hz), 1.40–1.70(2H,m), 3.65–3.80(2H,m), 5.62(1H,dd,J=16,8 Hz), 7.10–7.35(4H,m), 7.40–7.80(3H,m), 8.53(1H,dd,J=8,1 Hz), 9.40(1H,d,J=8 Hz).

2 9 I: 0.72(3H,t,J=7 Hz), 1.45–1.70(2H,m), 2.20(1H,d,J=4 Hz), 2.30–2.45(2H,m), 3.43(2H,s), 3.65–3.85(2H,m),3.75(3H,m), 4.46(1H,s), 5.10(1H,dd,J=16,7 Hz), 6.60(1H,dd,J=16,1 Hz), 7.10–7.50(5H,m), 7.70(1H,dd,J=8,1 Hz), 8.52(1H,dd,J=8,1 Hz).

3 0 L: 0.72(3H,t,J=7 Hz), 1.40–1.70(2H,m), 3.65–3.85(2H,m), 3.83(3H,s), 5.54(1H,dd,J=16, 8 Hz), 7.10–7.30(5H,m), 7.52(1H,t,J=8 Hz), 7.65 (1H,d,J=16 Hz), 8.17(1H,d,J=8 Hz), 9.36(1H,d,J=8 Hz).

3 0 I: 0.71(3H,t,J=7 Hz), 1.40–1.70(2H,m), 2.11(1H,d,J=4 Hz), 2.25–2.35(2H,m), 3.42(2H, s), 3.65–3.85(2H,m), 3.75(3H,s), 3.82(3H,s), 4.41(1H,b), 4.96(1H,dd,J=16,7 Hz), 6.61(1H,d, J=16 Hz), 7.05–7.30(5H,m), 7.46(1H,t,J=8 Hz), 8.16(1H,dd,J=8,1 Hz).

3 3 I: 2.52(2H,d,J=6 Hz), 2.83(2H,t-like,J=8 Hz), 3.45(2H,s), 3.76(3H,s), 3.97(2H,t-like,J=8 Hz), 4.50–4.60(1H,m), 5.50(1H,dd,J=16,6 Hz), 6.24(1H,d,J=16 Hz), 6.83(2H,d,J=8 Hz), 7.10–7.25(6H,m), 7.50–7.85(3H,m), 8.54(1H,d,J=8 Hz).

3 5 I: 2.52(2H,d like,J=6 Hz), 2.67(1H,d,J=4 Hz), 2.75–2.90(2H,m), 3.45(2H,s), 3.76(3H,s), 3.90–4.05(2H,m), 4.55(1H,b), 5.51(1H,dd,J=16,6 Hz), 6.25(1H,dd,J=16,1.4 Hz), 6.80–7.00(4H,m), 7.10–7.25(4H,m), 7.50–7.85(3H,m), 8.56(1H,d,J=7.6 Hz).

3 6 I: 2.29(3H,s), 2.51(2H,d like,J=5.9 Hz), 2.62(1H,d,J=3.8 Hz), 2.75-2.95(2H,m), 3.45(2H, s), 3.76(3H,s), 3.90-4.05(2H,m), 4.55(1H,bm), 5.51(1H,dd,J=16,6.2 Hz), 6.25(1H,dd,J=16,1.4 Hz), 6.80(2H,d,J=8 Hz), 7.02(2H,d,J=8 Hz), 7.10-7.30(4H,m), 7.50-7.85(3H,m), 8.56(1H,d,J=7.8 Hz).

3 7 I: 2.51(2H,d like,J=6.1 Hz), 2.63(1H,d,J=4.0 Hz), 2.80(2H,t like,J=8.0 Hz), 3.45(2H,s), 3.76(6H,s), 3.98(2H,t like,J=8.0 Hz), 4.54(1H, b), 5.50(1H,dd,J=16,6.0 Hz), 6.25(1H, dd,J=16,1.2 Hz), 6.70-6.85(4H,m), 7.10-7.25(4H,m), 7.50-7.80(3H,m), 8.56(1H,dd,J=7.0).

3 8 I: 2.49(2H,d like,J=5.7 Hz), 2.62(1H,d,J=4.0 Hz), 2.92(2H,t,J=7.4 Hz), 3.44(2H,s), 3.48(3H,s), 3.75(3H,s), 4.03(2H,t,J=7.4 Hz), 4.52(1H,bm), 5.45(1H,dd,J=16,6.2 Hz), 6.20(1H,dd,J=16,1.4 Hz), 6.65-7.25(8H,m), 7.50-7.80(3H,m), 8.57(1H,d,J=7.8 Hz).

3 9 I: 2.52(2H,d like,J=6.0 Hz), 2.63(1H,d,J=4.0 Hz), 2.87(2H,t like,J=8.0 Hz), 3.45(2H,s), 3.76(3H,s), 4.01(2H,t like,J=8.0 Hz), 4.55(1H, b), 5.51(1H,dd,J=16,6.0 Hz), 6.25(1H,dd,J=16,1.4 Hz), 6.55-6.75(2H,m), 6.80-6.95(1H,m), 7.10-7.30(5H,m), 7.50-7.85(3H,m), 8.56(1H,d,J=7.2 Hz).

4 0 I: 2.50(2H,d like,J=5.8 Hz), 2.65(1H,d,J=4.2 Hz), 2.94(2H,t like,J=7.8 Hz), 3.44(2H,s), 3.75(3H,s), 4.03(2H,t like,J=7.8 Hz), 4.54(1H, bm), 5.49(1H,dd,J=16,6.0 Hz), 6.23(1H,dd,J=16,1.4 Hz), 6.85-7.25(8H,m), 7.50-7.85(3H,m), 8.56(1H,d,J=8.0 Hz).

4 1 L: 3.20(3H,s), 3.58(2H,t,J=5.8 Hz), 4.05(2H,t,J=5.8 Hz), 6.36(1H,dd,J=16,7.6 Hz), 7.02(1H,d,J=16 Hz), 7.15-7.40(4H,m), 7.55-7.80(2H,m), 7.92(1H,d,J=8.2 Hz), 8.55(1H,dd,J=8.0,1.2 Hz), 9.36(1H,d,J=7.6 Hz).

4 1 I: 2.51(2H,d like,J=5.9 Hz), 2.66(1H,d,J=3.0 Hz), 3.19(3H,s), 3.45(2H,s), 3.56(2H,t,J=6.0 Hz), 3.75(3H,s), 4.04(2H,t,J=6.0 Hz), 4.53(1H,bs), 5.50(1H,dd,J=16,5.8 Hz), 6.23(1H,dd,J= 16,1.4 Hz), 7.10-7.35(4H,m), 7.48-7.80(3H,m), 8.51(1H,d,J=8.0 Hz).

4 2 L: 1.93(3H,s), 2.60-2.70(2H,m), 3.95-4.10(2H,m), 6.35(1H,dd,J=16,7.6 Hz), 7.05(1H, d,J=16 Hz), 7.20-7.80(6H,m), 7.92(1H,d, 8.4 Hz), 8.55(1H,d,J=8.0 Hz), 9.38(1H,d,J=7.6 Hz).

4 2 I: 1.91(3H,s), 2.52(2H,d like,J=6.0 Hz), 2.55-2.70(2H,m), 2.70(1H,d,J=4.0 Hz), 3.45(2H, s), 3.75(3H,s), 3.95-4.10(2H,m), 4.54(1H,bs), 5.51(1H,dd,J=16,6.0 Hz), 6.24(1H,dd, J=16,1.2 Hz), 7.15-7.35(4H,m), 7.45-7.85(3H,m), 8.50(1H,d,J=7.2 Hz).

4 3 I: 2.51(2H,d like,J=5.9 Hz), 2.61(1H,d,J=4.0 Hz), 3.44(2H,s), 3.75(3H,s), 4.40-4.60(3H, m), 4.81(1H,dd like,J=17,1.2 Hz), 5.07(1H,dd like,J=10,1.2 Hz), 5.50(1H,dd,J=16,6.0 Hz), 5.65-5.90(1H,m), 6.25(1H,dd,J=16,1.4 Hz), 7.10-7.30(4H,m), 7.48-7.85(3H,m), 8.53(1H,d like,J=8.2 Hz).

REFERENCE EXAMPLE 45

Step 1:
2-(2-Fluoroethyl)-3-(4-fluorophenyl)-1-(2H)-isoquinolinone

The compound (6.0 g) obtained by Reference Example III-1 was reacted with 2-fluoroethylamine and treated in the same way as in Step 1 of Reference Example IV to give the title compound (5.67 g) as colorless crystals.

mp 119°-121° C. (from diethyl ether-n-pentane).

Step 2:
1,2-Dihydro-2-(2-fluoroethyl)-3-(4-fluorophenyl)-1-oxoisoquinoline-4-carboxaldehyde The compound (1.50 g) obtained by Step 1 was reacted and treated in the same way as in Step 2 of Reference Example IV to give the title compound (1.04 g) as colorless crystals.

mp 132°-134° C. (from ethyl acetate-isopropyl ether).

Step 3: Ethyl (E)-3-[1,2-dihydro-2-(2-fluoroethyl)-3-(4-fluorophenyl)-1-oxo-4-isoquinolinyl]-2-propenoate (Compound 45D)

The compound (3.36 g) obtained by Step 2 was reacted and treated in the same way as in Step 3 of Reference Example IV to give the title compound (3.30 g) as colorless crystals.

mp 136°-137° C. (from ethyl acetate-isopropyl ether).

REFERENCE EXAMPLE 46

Step 1:
2-(2-Ethoxycarbonylethyl)-3-(4-fluorophenyl)-1-(2H)-isoquinolinone

The compound (5.0 g) obtained by Reference Example III-1 was reacted with 2-aminopropionitrile and treated in the same way as in Step 1 of Reference Example IV, and then a solution of the resulting product in ethanol was heated in the presence of conc. sulfuric acid to give the title compound (5.72 g) as colorless crystals.

mp 125°-126° C. (from diethyl ether-n-pentane).

Step 2:
1,2-Dihydro-2-(2-ethoxycarbonylethyl)-3-(4-fluorophenyl)-1-oxoisoquinoline-4-carboxyaldehyde The compound (3.2 g) obtained by Step 1 was reacted and treated in the same way as in Step 2 of Reference Example IV to give the title compound (2.5 g) as colorless crystals.

mp 71°-72° C. (from ethyl acetate-isopropyl ether-n-pentane)

Step 3:
1,2-Dihydro-2-(2-carboxyethyl)-3-(4-fluorophenyl)oxoisoquinoline-4-carboxyaldehyde The compound (2.47 g) obtained by Step 2 was hydrolyzed with sodium hydroxide in ethanol to give the title compound (2.07 g) as colorless crystals.

mp 204°-205° C. (from ethyl acetate-isopropyl ether).

Step 4:
1,2-Dihydro-2-[1-(N,N-dimethylcarbamoyl)ethyl]-3-(4-fluorophenyl)-1-oxoisoquinoline-4-carboxyaldehyde The compound (1.10 g) obtained by Step 3 was reacted with oxalyl chloride in tetrahydrofuran to give the acyl chloride, which was then treated with dimethylamine to give the title compound (0.98 g) as colorless crystals.

mp 154°-157° C. (from ethyl acetate-isopropyl ether).

Step 5: Ethyl (E)-3-{1,2-dihydro-2-[NN,N-dimethyl-carbamoyl)ethyl]-3-(4-fluorophenyl)-1-oxo-4-isoquinolinyl]-2-propenoate (Compound 46D)

The compound (900 mg) obtained by Step 4 was reacted and treated in the same way method as in Step 3 of Reference Example IV to give the title compound (840 mg) as colorless crystals.

mp 96°-98° C. (from ethyl acetate-isopropyl ether).

REFERENCE EXAMPLE 47 t-Butyl (E)-4-[3-(4-fluorophenyl)-1,2,5,6,7,8-hexahydro-2-(1-methylethyl)-1-oxo-4-isoquinolinyl]-5-hydroxy-3-oxo-6-heptenoate (47I)

REFERENCE EXAMPLE 48 t-Butyl (E)-7-[3-(4-fluorophenyl)-1,2,5,6,7,8-hexahydro-2-propyl-1-oxo-4-isoquinolinyl]-5-hydroxy-3-oxo-6-heptenoate (48I)

The production of two Compounds of Reference Examples 47 and 48 and their physiochemical properties are stated before.

REFERENCE EXAMPLE 49

Step 1: (S)-1,2,2-triphenyl-2-hydroxyethyl [3S(E)]-5-[1,2-dihydro-3-(4-fluorophenyl)-2-propyl-1-oxo-4-isoquinolinyl]-3-hydroxy-4-pentenoate In an atmosphere of argon gas, a solution of lithium diisopropylamide in n-hexane-tetrahydrofuran (21.2%) (2.80 ml) was added to a solution of (S)-2-acetoxy-1,1,2-triphenylethanol (520 mg) in anhydrous tetrahydrofuran (20 ml) at −78° C. under stirring. The mixture was stirred at 0° C. for 30 minutes and cooled to −90° C. A solution of Compound 16L (437 mg) in anhydrous tetrahydrofuran (5 ml) was added to the mixture taking 10 minutes and stirred at the same temperature for 30 minutes. The mixture was added to an aqueous ammonium chloride solution cooled to 0° C. and stirred at room temperature for 10 minutes and then extracted with ethyl acetate. The extract was washed with water, dried over anhydrous magnesium sulfate and distilled to remove the solvent. The residue was subjected to a silica gel column chromatography using ethyl acetate-n-hexane to give the title compound (630 mg) as colorless crystals.

mp 105° C. (from ethyl acetate-isopropyl ether).

IR$\nu_{max}^{Nujol}$ cm$^{-1}$: 3400, 1730, 1710, 1630, 1330, 1150.

NMR(200 MNz, CDCl$_3$)ppm: 0.72(3H,t,J=7.4 Hz), 1.4-1.7(2H, m), 2.23(2H, d-like,J=5.8 Hz), 2.40(1H,b), 2.85(1H,s), 3.6-3.8(2H,m), 4.30(1H,b), 5.39(1H,dd,J=16.0, 5.8 Hz), 6.09(1H,dd,J=16.0, 1.2 Hz), 6.71(1H,s), 6.95-7.75(22H,m), 8.51(1H,d,J=7.2 Hz).

Elemental Analysis for C$_{43}$H$_{38}$NO$_5$F: Calculated: C, 77.34; H, 5.74; N, 2.10. Found: C, 76.90; H, 5.90; N, 1.91. [α]$_D^{23}$=−78.5° (c=0.995, CH$_3$CN).

Step 2 Methyl [3S(E)]-5-[1,2-dihydro-3-(4-fluorophenyl)-2-propyl-1-oxo-4-isoquinolinyl]-3-hydroxy-4-pentenoate A solution of sodium methoxide in abs. methanol (4.1 mol, 0.4 ml) was added to a solution of the compound (1.02 g) obtained by Step 1 in abs. methanol (15 ml), followed by stirring for 15 minutes. The reaction mixture was neutralized with acetic acid under ice-cooling. After addition of ethyl acetate, the mixture was washed with water, sodium hydrogen carbonate solution, potassium hydrogen sulfate solutin and water in turn, dried over anhydrous magnesium sulfate and distilled to remove the solvent. The residue was subjected to a silica gel column chromatography using ethyl acetate-n-hexane to give the title compound (625 mg) as pale yellow oily substance.

IR$\nu_{max}^{Neat}$ cm$^{-1}$: 3400, 2950, 1735, 1630, 1590, 1570, 1475 1430, 1210, 1150.

NMR(200 MHz, CDCl$_3$)ppm: 0.72(3H,t,J=7.4 Hz), 1.45-1.65(2H,m), 2.32(2H,d, J=6.0 Hz), 2.91(1H,d,J=4.2 Hz), 3.60-3.85(2H,m), 3.70(3H,s), 4.47(1H,m), 5.54(1H,dd,J=16.0,6.2 Hz), 6.24(1H,d,J=16.0 Hz), 7.10-7.35(4H,m), 7.52(1H,t,J=7.6 Hz), 7.66(1H,t,J=7.0 Hz), 7.78(1H,d,J=7.6 Hz), 8.51(1H,d,J=7.8 Hz)

Step 3: t-Butyl [5S(E)]-4-[1,2-dihydro-3-(4-fluorophenyl)-2-propyl-1-oxo-4-isoquinolinyl]-4-hydroxy-3-oxo-6-heptenoate In an atmosphere of argon gas, a solution of lithium diisopopylamide in n-hexane and tetrahydrofuran (21.2%) (5.5 ml) was added to a solution of t-butyl acetate (0.81 ml) in anhydrous tetrahydrofuran (20 ml) at −78° C., followed by stirring for 20 minutes.

To the mixture was added a solution of the compound (581 mg) obtained by Step 2 in anhydrous tetrahydrofuran (3 ml). The mixture was stirred at −30° C. for 30 minutes and then added to aqueous saturated ammonium chloride solution under ice-cooling. After stirring at room temperature for 10 minutes, the mixture was extracted with ethyl acetate. The extract was washed with aqueous sodium hydrogen carbonate solution, aqueous potassium hydrogen sulfate solution and water in turn, dried over anhydrous magnesium sulfate and distilled to remove the solvent. The residue was subjected to a silica gel chromatography using ethyl acetate-n-hexane to give the title compound (530 mg) as colorless crystals.

mp 77°-79° C. (from ethyl acetate-isopropyl ether-n-pentane).

IR$\nu_{max}^{Nujol}$ cm$^{-1}$: 3350, 1730, 1710, 1615, 1570, 1500.

NMR(200 MHz, CDCl$_3$)ppm: 0.73(3H,t,J=7.4 Hz), 1.47(9H,s), 2.51(2H,d, J=5.8 Hz), 2.71(1H,d,J=4.2 Hz), 3.34(2H,s), 3.70-3.80(2H,m), 4.53(1H,m), 5.51(1H,dd,J=16, 6.0 Hz), 6.22(1H,dd,J=16,1.4 Hz), 7.10-7.30(4H,m), 7.48-7.80(3H,m), 8.51(1H,dd,J=6.8,0.6 Hz)

Elemental Analysis for C$_{29}$H$_{32}$NO$_5$F: Calculated: C, 70.57; H, 6.53; N, 2.84. Found: C, 70.32; H, 6.54; N, 2.74.

EXAMPLE 1-1

Methyl [3R*,5S*(E)]-7-[1,2-dihydro-3-(4-fluoro-2-methoxyphenyl)-2-(1-methylethyl)-1-oxo-4-isoquinolinyl]-3,5-dihydroxy-6-heptenoate In an atmosphere of argon gas, a solution of triethylborane in n-hexane (1M, 0.35 ml) was added to a mixture of anhydrous tetrahydrofuran (4 ml) and abs. methanol (1 ml) at room temperature for 25 minutes under stirring. The mixture was cooled at −70° C., and then to the mixture was added a solution of methyl (E)-7-[1,2-dihydro-3-(4-fluoro-2-methoxyphenyl)-2-(1-methylethyl)-1-oxo-4-isoquinolinyl]-5-hydroxy-3-oxo-6-heptenoate (Reference Example 1) (160 mg) in anhydrous tetrahydrofuran (1 ml) and abs. methanol (0.25 ml). After stirring at −70° C. for 25 minutes, the mixture to which sodium borohydride (16 mg) was added was stirred at the same temperature for an hour. The reaction mixture was added to a solution of 30% hydrogen peroxide (0.5 ml) and water (1.5 ml) at 0° C., followed by stirring for 10 minutes. The mixture was extracted with ethyl acetate. The extract was washed with sodium hydrosulfite solution and water, dried over anhydrous sodium sulfate and distilled to remove the solvent. The residue was subjected to a silica gel column chromatography, using ethyl acetate-n-hexane to give the title compound (145 mg) as colorless crystals.

mp 163°-165° C. (from ethyl acetate-diethyl ether)

IR$\nu_{max}^{Nujol}$cm$^{-1}$: 3400, 1735, 1630, 1600, 1505, 1440 1410, 1330, 1280.

NMR (200 MHz, CKCL$_3$)ppm: 1.2–1.5(2H,m), 1.45(3H,d,J=6.8 Hz), 1.59(3H,d, J=6.8 Hz), 2.45(2H,m), 2.94(1H,d,J=30 Hz), 3.62(1H,d,J=9 Hz), 3.74(3H,s), 3.80(3H,d,J=1.6 Hz), 3.97(1H,m), 4.11(1H,m), 4.34(1H,m), 5.51(1H,m), 6.18(1H,d,J−16 Hz), 6.74(2H,m), 7.07(1H,m), 7.45–7.75(3H,m), 8.49(1H,d,J=7.4 Hz).

EI-MS m/z: 483 (M+).

EXAMPLE 1-2

Sodium [3R*,5S*(E)]-7-[1,2-dihydro-3-(4-fluoro-2-methoxyphenyl-2-(1-methylethyl)-1-oxo-4-isoquinolinyl]-3,5-dihydroxy-6-heptenoate 1N-Sodium hydroxide (0.165 ml) was added to a solution of methyl [3R*,5S*(E)]-7-[1,2-dihydro-3-(4-fluoro-2-methoxyphenyl)-2-(1-methylethyl)-1-oxo-4-isoquinolinyl]-3,5-dihydroxy-6-heptenoate (Example 1-1) (84 mg) in methanol (2.0 ml) at room temperature under stirring. The reaction mixture was stirred at room temperature for an hour and distilled to remove the solvent. The residue to which water was added was washed with ethyl acetate, and the aqueous layer was concentrated. The concentrate was lyophilized to give the title compound (74 mg) as white powder.

IR$_{max}^{KBr}$cm$^{-1}$: 3400, 2930, 1640, 1600, 1580, 1500, 1405, 1330, 1280.

NMR (200 MHz, D$_2$O)ppm: ca 1.4(2H,m), 1.39(3H,d,J=7 Hz), 1.52(3H,d,J=7 Hz), 2.27(2H,m), 3.40–3.63(each 0.5H,m), 3.85(3H,s), 4.15(1H,m), 4.24(1H,m), 5.50(1H,m), 6.27,6.31 (each 1H,d,J-16 Hz), 6.87–7.05(2H,m), 7.17(1H,m), 7.60(1H,m), 7.79(2H,m), 8.28(1H,d,J-8 Hz)

Elemental Analysis for C$_{26}$H$_{27}$NO$_6$FNa.3.5H$_2$O: Calculated: C, 56.31; H, 6.18; N, 2.53. Found: C, 56.44; H, 5.85; N, 2.56.

EXAMPLE 1-3

[4α,6β(E)]-6-{2-[1,2-Dihydro-3-(4-fluoro-2-methoxyphenyl)-2-(1-methylethyl)-1-oxo-r-isoquinolinyl]ethenyl}-4-hydroxy-3,4,5,6-tetrahydro-2H-pyran-2-one 1N-Sodium hydroxide solution (0.12 ml) was added to a solution of methyl [3R*,5S*(E)]-7-[1,2-dihydro-3-(4-fluoro-2-methoxyphenyl)-2-(1-methylethyl)-1-oxo-4-isoquinolinyl]-3,5-dihydroxy-6-heptanoate (Example 1-1) (48 mg) in methanol (2 ml) at room temperature under stirring. The reaction mixture was stirred at room temperature for 30 minutes and distilled to remove the solvent. The residue to which water was added was washed with ethyl acetate. The aqueous layer was acidified with 1N-hydrochloric acid and extracted with ethyl acetate. The extract was washed with water, dried over anhydrous sodium sulfate and distilled to remove the solvent to give [3R*,5S*(E)]-7-[1,2-dihydro-3-(4-fluoro-2-methoxyphenyl)-2-(1-methylethyl)-1-oxo-4-isoquinolinyl]-3,5-dihydroxy-6-heptenoic acid as colorless oily substance. This oily substance was dissolved in a mixture of benzene (5 ml) and tetrahydrofuran (1 ml). The mixture was refluxed for 20 minutes in an apparatus with water separator. The reaction mixture to which ethyl acetate was added was washed with sodium hydrogen carbonate solution and water in turn, dried over anhydrous sodium sulfate and distilled to remove the solvent. The residue was subjected to a silica gel column chromatography, using ethyl acetate - n-hexane to give the title compound (10 mg) as colorless crystals.

IR$\nu_{max}^{Neat}$cm$^{-1}$: 3400, 1740, 1640, 1610, 1505, 1410, 1330, 1280, 1240, 1150.

NMR(200 MHz, CDCl$_3$)ppm: ca 1.3(2H,m), 1.45(3H,d,J=7 Hz), 1.57(3H,d,J=7 Hz), 2.65(2H,m), 3.80(3H,s), 3.96(1H,m), 4.23(1H,m), 5.10(1H,m), 5.58(1H,m), 6.23(1H,d,J-16 Hz), 6.76(2H,m), 7.06(1H,m), 7.44–7.76(3H,m), 8.49(1H, d,J=8 Hz).

EI-MS m/z: 451(M+).

EXAMPLE 2-1

Methyl [3R*,5S*(E)]-7-[1,2-dihydro-3-(4-fluorophenyl)-2-(1-methylethyl)-1-oxo-4-isoquinolinyl]-3,5-dihydroxy-6-heptenoate The compound obtained by Reference Example 2 was reacted and treated in the same way as in Example 1-1 to give the title compound as colorless crystals.

mp 151°-152° C. (from ethyl acetate-n-hexane).

IR$\nu_{max}^{Nujol}$cm$^{-1}$: 3400, 1725, 1640, 1600, 1505, 1320, 1220, 1155.

NMR(200 MHz, CDCL$_3$)ppm: 1.3(2H,m), 1.52(6H,d,J-7 Hz), 2.45(2H,m), 2.03(1H,b), 3.57(1H,b), 3.74(3H,s), 4.03(1H,m), 4.1(1H,m), 4.3(1H,m), 5.50(1H,dd,J=16.6 Hz), 6.14(1H,d,J-16 Hz), 7.2(4H,m), 7.50(1H,t-like, J=7 Hz), 7.65(1H,t-like,J=7 Hz), 7.76(1H,d,J=8 Hz), 8.48(1H,dd,J=8.1 Hz).

EI-MS m/z: 453(M+).

EXAMPLE 2-2

Sodium [3R*,5S*(E)]-7-[1,2-dihydro-3-(4-fluorophenyl)-2-(1-methylethyl)-1-oxo-4-isoquinolinyl]-3,5-dihydroxy-6-heptenoate The compound obtained by Example 2-1 was reacted and treated in the same method as in Example 1-2 to give the title compound as white powder.

IR$\nu_{max}^{KBr}$cm$^{-1}$: 3400, 1645, 1605, 1570, 1505, 1485, 1400, 1325, 1220.

NMR(200 MHz, D$_2$O)ppm: 1.25–1.68(2H,m), 1.44(6H,d,J-7 Hz), 2.27(2H,m), 3.54(1H,m), 4.10–4.30(2H,m), 5.43(1H,dd, J=16.7 Hz), 6.17(1H,d,J=16 Hz), 7.25–7.40(4H,m), 7.51–7.65(1H,m), 7.66–7.81(2H,m), 8.25(1H,d, J=8 Hz).

EXAMPLE 3-48

The compounds obtained by Reference Examples 3–48 were reacted and treated in the same way as in Examples 1-1 and 1-2 to give the corresponding compounds 3–48-1 (esters) and -2 (sodium salts) (Reaction Scheme 6). Some physicochemical properties of their compounds are shown in Table 5. The sodium salts thereof were lyophilized to give white powder (melting point of the compounds were unmeasured). In the table, the ring A for Compounds 3–46 means

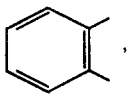

and the ring A for Compounds 47 and 48 means

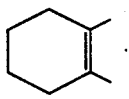

Reaction Scheme 6

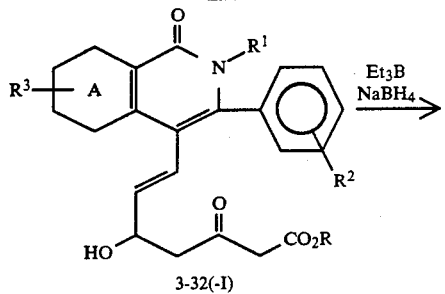

-continued
Reaction Scheme 6

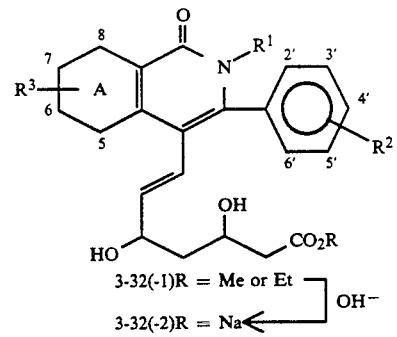

3-32(-1) R = Me or Et
3-32(-2) R = Na ← OH⁻

TABLE 5

| Example No. | $R^1$ | $R^2$ | $R^3$ | R | mp (°C.) |
|---|---|---|---|---|---|
| 3-1 | —CHMe₂ | 2'-F, 4'-MeO | H | Me | 102–104 |
| 3-2 | " | " | " | Na | — |
| | NMR(200MHz, D₂O)ppm: 1.14–1.68(2H, m), 1.42(3H, d, J= 7Hz), 1.49(3H, d, J=7Hz), 2.10–2.38(2H, m), 3.46–3.77 (1H, m), 3.90(3H, s), 4.07–4.35(2H, m), 5.39–5.58(1H, m), 6.26(1H, dd, J=16.4Hz), 6.82–7.03(2H, m), 7.08– 7.28(1H, m), 7.47–7.85(3H, m), 8.24(1H, d, J=8Hz) | | | | | |
| 4-1 | —CHMe₂ | 2'-MeO, 5'-F | H | Me | 142–144 |
| 4-2 | " | " | " | Na | — |
| | NMR(200MHz, D₂O)ppm: 1.16–1.69(2H, m), 1.43(3H, d, J= 7Hz), 1.53(3H, d, J=7Hz), 2.15–2.36(2H, m), 3.27–3.44 (0.4H, m), 3.50–3.68(0.6H, m), 3.84(3H, s), 4.01–4.37 (2H, m), 5.40–5.66(1H, m), 6.34(0.6H, d, J=16Hz), 6.36 (0.4H, d, J=16Hz), 7.00–7.42(3H, m), 7.55–7.94(3H, m), 8.30(1H, d, J=8Hz) | | | | | |
| 5-1 | —CHMe₂ | 2'-Me, 4'-F | H | Me | 142–144 |
| 5-2 | " | " | " | Na | — |
| | NMR(200MHz, D₂O)ppm: 1.24–1.78(8H, m), 2.08(1.5H, s), 2.09(1.5H, s), 2.26(2H, d, J=7Hz), 3.40–3.64(1H, m), 4.06(1H, m), 4.12–4.34(1H, m), 5.39–5.60(1H, m), 6.18 (1H, t-like, J=16Hz), 7.00–7.34(3H, m), 7.49–7.65(1H, m), 7.66–7.92(2H, m), 8.29(1H, d, J=8Hz) | | | | | |
| 6-1 | —CHMe₂ | 2'-F, 4'-F | H | Me | 132–134 |
| 6-2 | " | " | " | Na | — |
| | NMR(200MHz, D₂O)ppm: 1.21–1.70(2H, m), 1.43(3H, d, J= 7Hz), 1.50(3H, d, J=7Hz), 2.13–2.44(2H, m), 3.47–3.77 (1H, m), 4.00–4.24(1H, m), 4.23(1H, m), 5.39–5.68(1H, m), 6.22(1H, dd, J=16.4Hz), 7.06–7.42(3H, m), 7.44– 7.83(3H, m), 8.19(1H, d, J=8Hz) | | | | | |
| 7-1 | —CHMe₂ | 4'-F | 6-Me | Me | 150–152 |
| 7-2 | " | " | " | Na | — |
| | NMR(200MHz, D₂O)ppm: 1.19–1.67(2H, m), 1.42(6H, d, J= 6Hz), 2.26(2H, m), 2.45(3H, s), 3.41–3.60(1H, m), 4.03– 4.29(2H, m), 5.38(1H, dd, J=16.7Hz), 6.15(1H, d, J=16 Hz), 7.18–7.50(5H, m), 7.57(1H, s), 8.17(1H, d, J=8Hz) | | | | | |
| 8-1 | —CHMe₂ | 4'-F | 6-Me, 7-Me | Me | 147–149 |
| 8-2 | " | " | " | Na | — |
| | NMR(200MHz, D₂O)ppm: 1.18–1.68(2H, m), 1.42(6H, d, J= 7Hz), 2.30(3H, s), 2.62(3H, s), 2.09–2.42(2H, m), 3.41– 3.60(1H, m), 4.03–4.28(2H, m), 5.37(1H, dd, J=16.7Hz), 6.11(1H, d, J=16Hz), 7.10–7.39(4H, m), 7.45(1H, s) | | | | | |
| 9-1 | —CHMe₂ | 4'-F | 6-F | Me | 137–138 |
| 9-2 | " | " | " | Na | — |
| | NMR(200MHz, D₂O)ppm: 0.99–1.32(2H, m), 1.43(6H, d, J= 6Hz), 2.05–2.35(2H, m), 3.34–3.57(1H, m), 3.99–4.30 (2H, m), 5.18(1H, d, J=16Hz), 6.40(1H, dd, J=16.9Hz), | | | | | |

TABLE 5-continued

| Example No. | R¹ | R² | R³ | R | mp (°C.) |
|---|---|---|---|---|---|
| | 7.18–7.67(6H, m), 8.05(1H, d, J=8Hz) | | | | |
| 10-1 | —(CH₂)₂Me | 2'-Me, 4'-F | H | Me | 110–111 |
| 10-2 | " | " | " | Na | — |
| | NMR(200MHz, D₂O)ppm: 0.67(3H, t, J=7Hz), 1.3–1.6(4H, m), 2.02(3H, s), 2.25(2H, m), 3.3–3.6(2H, m), 4.0(1H, m), 4.25(1H, m), 5.45(1H, dd, J=16, 7Hz), 6.20, 6.27 (total 1H, each d, J=16Hz), 7.14(3H, m), 7.6(1H, m), 7.8(2H, m), 8.34(1H, d, J=8Hz) | | | | |
| 11-1 | —(CH₂)₂Me | 2'-F, 4'-F | H | Me | 92–94 |
| 11-2 | " | " | " | Na | — |
| | NMR(200MHz, D₂O)ppm: 0.69(3H, t, J=7Hz), 1.16–1.71 (4H, m), 2.08–2.45(2H, m), 3.39–3.95(3H, m), 4.13–4.33 (1H, m), 5.33–5.34(1H, m), 6.23(1H, d, J=16Hz), 6.98–7.40(3H, m), 7.42–7.81(3H, m), 8.19(1H, dd, J=7.1Hz) | | | | |
| 12-1 | —(CH₂)₂Me | 4'-F | 8-Me | Me | 136–137 |
| 12-2 | " | " | " | Na | — |
| | NMR(200MHz, D₂O)ppm: 0.65(3H, t, J=7Hz), 1.1–1.6(4H, m), 2.21(2H, m), 2.77(3H, s), 3.3–3.6(3H, m), 4.18(1H, m), 5.24(1H, dd, J=16, 7Hz), 6.09(1H, d, J=16Hz), 7.2(5H, m), 7.46(2H, m) | | | | |
| 13-1 | —(CH₂)₂—Ph | 4'-F | H | Me | 143–145 |
| 13-2 | " | " | " | Na | — |
| | NMR(200MHz, D₂O)ppm: 1.10–1.35(1H, m), 1.40–1.65(1H, m), 2.00–2.60(4H, m), 3.30–3.75(3H, m), 4.05–4.30(1H, m), 5.31(1H, dd, J=16, 7Hz), 6.09(1H, d, J=16Hz), 6.50–7.30(12H, m), 8.19(1H, d, J=8Hz) | | | | |
| 14-1 | Me | 4'-F | H | Et | oily |
| | NMR(200MHz, CDCl₃)ppm: 1.29(3H, t, J=7Hz), 1.30–1.60 (2H, m), 2.43(2H, m), 3.17(1H, d, J=2Hz), 3.30(3H, s), 3.62(1H, m), 4.12(1H, b), 4.19(2H, q, J=7Hz), 4.36(1H, b), 5.52(1H, dd, J=16, 6Hz), 6.27(1H, dd, J=16, 1Hz), 7.10–7.30(4H, m), 7.45–7.85(3H, m), 8.53(1H, dd, J=8, 1Hz) | | | | |
| 14-2 | Me | 4'-F | H | Na | — |
| | NMR(200MHz, D₂O)ppm: 1.31(1H, m), 1.59(1H, m), 2.26 (2H, m), 3.20(3H, s), 3.52(1H, m), 4.22(1H, m), 5.36(1H, ddd, J=16, 7, 1Hz), 6.17(1H, d, J=16Hz), 7.15–7.35(4H, m), 7.45–7.80(3H, m), 8.18(1H, d, J=8Hz) | | | | |
| 15-1 | Et | 4'-F | H | Me | 120–123 |
| 15-2 | " | " | " | Na | — |
| | NMR(200MHz, D₂O)ppm: 1.04(3H, t, J=6Hz), 1.31(1H, m), 1.58(1H, m), 2.26(2H, d, J=6Hz), 3.50(1H, b), 3.60–3.95 (2H, m), 4.10–4.35(1H, m), 5.37(1H, dd, J=16, 7Hz), 6.14 (1H, d, J=16Hz), 7.10–7.85(7H, m), 8.22(1H, d, J=7Hz) | | | | |
| 16-1 | —(CH₂)₂Me | 4'-F | H | Et | 112–114 |
| 16-2 | " | " | " | Na | — |
| | NMR(200MHz, D₂O)ppm: 0.67(3H, t, J=7Hz), 1.20–1.70 (4H, m), 2.26(2H, d, J=6Hz), 3.50(1H, b), 3.60–3.80(2H, m), 4.15–4.30(1H, m), 5.41(1H, dd, J=16, 7Hz), 6.20(1H, d, J=16Hz), 7.15–7.45(4H, m), 7.50–7.90(3H, m), 8.28 (1H, d, J=8Hz) | | | | |
| 17-1 | —(CH₂)₃Me | 4'-F | H | Me | 104–105 |
| 17-2 | " | " | " | Na | — |
| | NMR(200MHz, D₂O)ppm: 0.63(3H, t, J=7Hz), 0.90–1.65 (6H, m), 2.25(2H, d, J=5Hz), 3.35–3.75(3H, m), 4.10–4.30(1H, m), 5.31(1H, dd, J=16, 7Hz), 6.09(1H, d, J=16 Hz), 7.00–7.30(4H, m), 7.40–7.75(3H, m), 8.19(1H, d, J=8Hz) | | | | |
| 18-1 | —(CH₂)₄Me | 4'-F | H | Me | 109–112 |
| 18-2 | " | " | " | Na | — |
| | NMR(200MHz, D₂O)ppm: 0.60–0.85(3H, m), 0.85–1.15 (4H, m), 1.15–1.65(4H, m), 2.25(2H, d, J=5Hz), 3.40–3.75(3H, m), 4.10–4.30(1H, m), 5.36(1H, dd, J=16, 7Hz), 6.15(1H, d, J=16Hz), 7.10–7.35(4H, m), 7.45–7.80(3H, m), 8.24(1H, d, J=8Hz) | | | | |
| 19-1 | —(CH₂)₆Me | 4'-F | H | Me | 87–89 |
| 19-2 | " | " | " | Na | — |
| | NMR(200MHz, D₂O)ppm: 0.72(3H, t, J=6Hz), 0.80–1.70 (12H, m), 2.25(2H, m), 3.62(3H, m), 4.16(1H, m), 5.36(1H, dd, J=16, 6Hz), 6.08(1H, d, J=16Hz), 7.00–7.30(3H, m), 7.40–7.55(1H, m), 7.55–7.90(3H, m), 8.20–8.40(1H, m) | | | | |
| 20-1 | —(CH₂)₈Me | 4'-F | H | Me | 98–101 |
| 20-2 | " | " | " | Na | — |
| | NMR(200MHz, D₂O)ppm: 0.72(3H, t, J=7Hz), 0.80–1.65 (16H, m), 2.00–2.40(2H, m), 3.52(2H, m), 3.80(1H, b), 4.08(1H, b), 5.29(1H, dd, J=15, 6Hz), 5.93(1H, d, J=15 Hz), 6.90–7.80(7H, m), 8.23(1H, d, J=7Hz) | | | | |
| 21-1 | —CH₂CHMe₂ | 4'-F | H | Me | oily |
| | NMR(200MHz, CDCl₃)ppm: 0.72(6H, d, J=7Hz), 1.20–1.60 (2H, m), 1.92(1H, m), 2.45(2H, m), 3.08(1H, d, J=1Hz), | | | | |

TABLE 5-continued

| Example No. | R¹ | R² | R³ | R | mp (°C.) |
|---|---|---|---|---|---|
| | 3.59(1H, d, J=2Hz), 3.65-3.90(2H, m), 3.73(3H, s), 4.10 (1H, b), 4.35(1H, b), 5.49(1H, dd, J=16, 6Hz), 6.21(1H, d, J=16Hz), 7.05-7.35(4H, m), 7.45-7.85(3H, m), 8.51(1H, d, J=8Hz) | | | | |
| 21-2 | CH₂CHMe₂ | 4'-F | H | Na | — |
| | NMR(200MHz, D₂O)ppm: 0.62(6H, d, J=7Hz), 1.20-1.40 (1H, m), 1.45-1.90(2H, m), 2.26(2H, m), 3.55(1H, b), 3.71(2H, d, J=7Hz), 4.15-4.30(1H, m), 5.37(1H, dd, J=16, 7Hz), 6.15(1H, d, J=16Hz), 7.10-7.40(4H, m), 7.50-7.85(3H, m), 8.26(1H, d, J=8Hz) | | | | |
| 22-1 | ▷ (cyclopropyl) | 4'-F | H | Et | oily |
| | NMR(200MHz, CDCl₃)ppm: 0.50-0.65(2H, m), 0.75-0.85 (2H, m), 1.29(3H, t, J=7Hz), 1.20(2H, m), 2.45(2H, m), 2.70-2.85(1H, m), 3.27(1H, d, J=2Hz), 3.69(1H, d, J=2 Hz), 4.14(1H, b), 4.19(2H, q, J=7Hz), 4.37(1H, b), 5.50 (1H, dd, J=16, 6Hz), 6.31(1H, dd, J=16, 1Hz), 7.05-7.35 (4H, m), 7.48-7.85(3H, m), 8.48(1H, dd, J=8, 2Hz) | | | | |
| 22-2 | ▷ (cyclopropyl) | 4'-F | H | Na | — |
| | NMR(200MHz, D₂O)ppm: 0.35-0.55(2H, m), 0.65-0.90(2H, m), 1.30-1.50(1H, m), 1.50-1.75(1H, m), 2.29(2H, d, J=7Hz), 2.81(1H, b), 3.64(1H, b), 4.15-4.35(1H, m), 5.40 (1H, dd, J=16, 7Hz), 6.25(1H, d, J=16Hz), 7.15-7.40(4H, m), 7.45-7.80(3H, m), 8.16(1H, d, J=8Hz) | | | | |
| 23-1 | cyclohexyl | 4'-F | H | Me | 124-127 |
| 23-2 | " | " | " | Na | — |
| | NMR(200MHz, D₂O)ppm: 0.65-1.80(10H, m), 2.10-2.60 (4H, m), 3.40-3.70(2H, m), 4.15-4.30(1H, m), 5.39(1H, dd, J=16, 8Hz), 6.14(1H, d, J=16Hz), 7.05-7.35(4H, m), 7.45-7.80(3H, m), 8.23(1H, d, J=8Hz) | | | | |
| 24-1 | —CH₂—(phenyl) | 4'-F | H | Me | 126-129 |
| 24-2 | " | " | " | Na | — |
| | NMR(200MHz, D₂O)ppm: 1.10-1.40(1H, m), 1.40-1.70(1H, m), 2.22(2H, d, J=6Hz), 3.46(1H, b), 4.10-4.35(1H, m), 5.07(2H, s), 5.44(1H, dd, J=16, 6Hz), 6.23(1H, d, J=16 Hz), 6.65-7.40(9H, m), 7.45-8.00(3H, m), 8.33(1H, d, J=8Hz) | | | | |
| 25-1 | —(phenyl)—F | 4'-F | H | Me | 178-180 |
| 25-2 | " | " | " | Na | — |
| | NMR(200MHz, D₂O)ppm: 1.20-1.40(1H, m), 1.50-1.70(1H, m), 2.22(2H, d, J=6Hz), 3.47(1H, b), 4.20-4.35(1H, m), 5.53(1H, dd, J=16, 7Hz), 6.41(1H, d, J=16Hz), 6.85-7.25 (8H, m), 7.60-7.80(1H, m), 7.80-8.00(2H, m), 8.34(1H, d, J=8Hz) | | | | |
| 26-1 | —CHMe₂ | 4'-F | 5-Me | Me | 164-165 |
| 26-2 | " | " | " | Na | — |
| | NMR(200MHz, D₂O)ppm: 1.00-1.20(1H, m), 1.25-1.50 (1H, m), 1.41(6H, d, J=6Hz), 2.10-2.35(2H, m), 2.44(3H, s), 3.54(1H, b), 3.95-4.20(2H, m), 5.02(1H, dd, J=16, 7Hz), 6.29(1H, d, J=16Hz), 7.10-7.50(6H, m), 8.14(1H, d, J=7Hz) | | | | |
| 27-1 | —(CH₂)₂Me | 4'-F | 5-Me | Me | 113-115 |
| 27-2 | " | " | " | Na | — |
| | NMR(200MHz, D₂O)ppm: 0.65(3H, t, J=7Hz), 0.95-1.20 (1H, m), 1.25-1.60(3H, m), 2.15-2.35(2H, m), 2.51(3H, | | | | |

TABLE 5-continued

| Example No. | R¹ | R² | R³ | R | mp (°C.) |
|---|---|---|---|---|---|
| | s), 3.50(1H, b), 3.65(2H, m), 4.05-4.20(1H, m), 5.06(1H, dd, J=16, 7Hz), 6.35(1H, d, J=16Hz), 7.10-7.55(6H, m), 8.19(1H, d, J=7, 6Hz) | | | | |
| 28-1 | —(CH₂)₂Me | 4'-F | 5-F | Me | oily |
| | NMR(200MHz, CDCl₃)ppm: 0.72(3H, t, J=7Hz), 1.10-1.65 (4H, m), 2.41(2H, m), 2.56(1H, d, 2Hz), 3.54(1H, d, J=3 Hz), 3.65-3.80(2H, m), 3.73(3H, s), 4.05(1H, b), 4.26 (1H, b), 5.18(1H, dd, J=16, 7Hz), 6.44(1H, ddd, J=16, 9, 1Hz), 7.10-7.50(6H, m), 8.33(1H, dd, J=8, 1Hz) | | | | |
| 28-2 | —(CH₂)₂Me | 4'-F | 5-F | Na | — |
| | NMR(200MHz, D₂O)ppm: 0.66(3H, t, J=7Hz), 1.00-1.25 (1H, m), 1.25-1.60(3H, m), 2.10-2.35(2H, m), 3.43(1H, b), 3.50-3.75(2H, m), 4.05-4.25(1H, m), 5.11(1H, dd, J= 16, 7Hz), 6.30(1H, dd, J=16, 9Hz), 7.10-7.55(6H, m), 7.97 (1H, d, J=8Hz) | | | | |
| 29-1 | —(CH₂)₂Me | 4'-F | 5-Cl | Me | oily |
| | NMR(200MHz, CDCl₃)ppm: 0.71(3H, t, J=7Hz), 1.10-1.65 (4H, m), 2.35-2.65(3H, m), 3.56(1H, b), 3.65-3.80(2H, m), 3.73(3H, s), 4.07(1H, b), 4.27(1H, b), 5.08(1H, dd, J=16, 7Hz), 6.57(1H, dd, J=16, 1Hz), 7.10-7.30(4H, m), 7.35-7.45(1H, m), 7.69(1H, dd, J=8, 2Hz), 8.51(1H, dd, J=8, 2 Hz) | | | | |
| 29-2 | —(CH₂)₂Me | 4'-F | 5-Cl | Na | — |
| | NMR(200MHz, D₂O)ppm: 0.66(3H, t, J=7Hz), 1.00-1.20 (1H, m), 1.25-1.60(3H, m), 2.10-2.40(2H, m), 3.52(1H, b), 3.67(2H, b), 4.05-4.25(1H, m), 5.04(1H, dd, J=16, 7 Hz), 6.50(1H, d, J=16Hz), 7.15-7.50(5H, m), 7.69(1H, d, J=7Hz), 8.21(1H, d, J=8Hz) | | | | |
| 30-1 | —(CH₂)₂Me | 4'-F | 5-MeO | Me | oily |
| | NMR(200MHz, CDCl₃)ppm: 0.70(3H, t, J=7Hz), 1.05-1.65 (4H, m), 2.25(1H, b), 2.35-2.45(2H, m), 3.56(1H, d, J=2 Hz), 3.65-3.80(2H, m), 3.72(3H, s), 3.82(3H, s), 4.02 (1H, b), 4.21(1H, b), 4.96(1H, dd, J=16, 7Hz), 6.58(1H, dd, J=16, 1Hz), 7.05-7.30(5H, m), 7.45(1H, t, J=8Hz), 8.15(1H, dd, J=8, 1Hz) | | | | |
| 30-2 | —(CH₂)₂Me | 4'-F | 5-MeO | Na | — |
| | NMR(200MHz, D₂O)ppm: 0.63(3H, t, J=7Hz), 1.00-1.20 (1H, m), 1.25-1.55(3H, m), 2.10-2.35(2H, m), 3.40-3.80 (3H, m), 3.80(3H, s), 4.00-4.20(1H, m), 6.42(1H, d, J=16 Hz), 7.05-7.40(5H, m), 7.48(1H, t, J=8Hz), 7.90(1H, d, J= 8Hz), (one elefinic H; overlapped with D₂O) | | | | |
| 31-1 | —CHMe₂ | 4'-Me | H | Et | 150-152 |
| 31-2 | " | " | " | Na | — |
| | NMR(200MHz, D₂O)ppm: 1.10-1.65(2H, m), 1.39(6H, d, J= 7Hz), 2.22(2H, d, J=6Hz), 2.41(3H, s), 3.51(1H, b), 4.00-4.25(2H, m), 5.38(1H, dd, J=16, 7Hz), 6.13(1H, d, J=16 Hz), 7.00-7.80(7H, m), 8.22(1H, d, J=8Hz) | | | | |
| 32-1 | 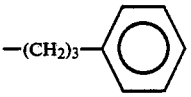—(CH₂)₃— | 4'-F | H | Me | 129-131 |
| 32-2 | " | " | " | Na | — |
| | NMR(200MHz, D₂O)ppm: 1.00-1.65(4H, m), 2.00-2.40 (4H, m), 3.15-3.70(3H, m), 4.00-4.20(1H, m), 5.19(1H, dd, J=16, 6Hz), 5.94(1H, d, J=16Hz), 6.50-7.20(9H, m), 7.30-7.75(3H, m), 8.20(1H, d, J=8Hz) | | | | |
| 33-1 | 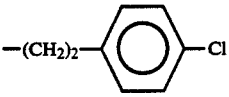—(CH₂)₂—⬡—Cl | 4'-F | H | Me | 153-155 |
| 33-2 | " | " | " | Na | — |
| | NMR(200MHz, D₂O)ppm: 0.95-1.15(1H, m), 1.20-1.50 (1H, m), 1.65-2.10(2H, m), 2.77(2H, t-like, J=8Hz), 3.46(1H, b), 3.85(2H, t-like, J=8Hz), 4.00-4.15(1H, m), 5.47(1H, dd, J=16, 6Hz), 6.08(1H, d, J=16Hz), 6.88 (2H, d, J=8Hz), 7.15-7.70(7H, m), 7.70-7.95(2H, m) | | | | |
| 34-1 | 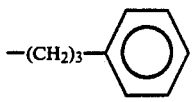—(CH₂)₃— | 4'-F | H | Me | 129-131 |
| 34-2 | " | " | " | Na | — |

TABLE 5-continued

| Example No. | R¹ | R² | R³ | R | mp (°C.) |
|---|---|---|---|---|---|
| | NMR(200MHz, D₂O)ppm: 1.00-1.65(4H, m), 2.00-2.40(4H, m), 3.15-3.70(3H, m), 4.00-4.20(1H, m), 5.19(1H, dd, J=16, 6.2Hz), 5.94(1H, d, J=16Hz), 6.50-7.20(9H, m), 7.30-7.75(3H, m), 8.20(1H, d, J=7.8Hz) | | | | |
| 35-1 | —(CH₂)₂—C₆H₄—F | 4'-F | H | Me | 122-123 |
| 35-2 | " | " | " | Na | — |
| | NMR(200MHz, D₂O)ppm: 1.24(1H, m), 1.54(1H, m), 2.05-2.50(4H, m), 3.35-3.70(3H, m), 4.10-4.25(1H, m), 5.30 (1H, dd, J=16, 7.0Hz), 6.09(1H, d, J=16Hz), 6.50-7.70(11H, m), 8.17(1H, d, J=7.4Hz) | | | | |
| 36-1 | —(CH₂)₂—C₆H₄—Me | 4'-F | H | Me | 147-150 |
| 36-2 | " | " | " | Na | — |
| | NMR(200MHz, D₂O)ppm: 1.30(1H, m), 1.55(1H, m), 2.11 (3H, s), 2.15-2.60(4H, m), 3.40-3.80(3H, m), 4.10-4.30 (1H, m), 5.36(1H, dd, J=16, 7.0Hz), 6.16(1H, d, J=16Hz), 6.58(2H, d, J=7.8Hz), 6.80-7.00(4H, m), 7.05-7.25(2H, m), 7.40-7.80(3H, m), 8.27(1H, d, J=7.4Hz) | | | | |
| 37-1 | —(CH₂)₂—C₆H₄—OMe | 4'-F | H | Me | 131-133 |
| 37-2 | " | " | " | Na | — |
| | NMR(200MHz, D₂O)ppm: 1.24(1H, m), 1.53(1H, m), 2.10-2.35(4H, m), 3.30-3.60(3H, m), 3.48(3H, s), 4.10-4.25 (1H, m), 5.28(1H, dd, J=16, 7.0Hz), 6.07(1H, d, J=16Hz), 6.40-6.60(4H, m), 6.70-6.90(2H, m), 7.00-7.70(5H, m), 8.17(1H, d, J=7.6Hz) | | | | |
| 38-1 | —(CH₂)₂—C₆H₄(2-OMe) | 4'-F | H | Me | 108-110 |
| 38-2 | " | " | " | Na | — |
| | NMR(200MHz, D₂O)ppm: 1.22(1H, m), 1.54(1H, m), 2.10-2.45(4H, m), 3.16(3H, s), 3.40-3.65(3H, m), 4.05-4.25 (1H, m), 5.26(1H, dd, J=16, 7.0Hz), 6.01(1H, d, J=16Hz), 6.45-6.75(5H, m), 6.90-7.15(3H, m), 7.25-7.70(3H, m), 8.20(1H, d, J=7.8Hz) | | | | |
| 39-1 | —(CH₂)₂—C₆H₄(3-F) | 4'-F | H | Me | 138-139 |
| 39-2 | " | " | " | Na | — |
| | NMR(200MHz, D₂O)ppm: 1.23(1H, m), 1.54(1H, m), 2.10-2.50(4H, m), 3.40-3.70(3H, m), 4.10-4.25(1H, m), 5.30 (1H, dd, J=16, 7.2Hz), 6.08(1H, d, J=16Hz), 6.20-6.45(2H, m), 6.60-6.75(1H, m), 6.80-7.20(5H, m), 7.25-7.70(3H, m), 8.17(1H, d, J=7.8Hz) | | | | |
| 40-1 | —(CH₂)₂—C₆H₄(2-F) | 4'-F | H | Me | 115-117 |
| 40-2 | " | " | " | Na | — |

TABLE 5-continued

| Example No. | R¹ | R² | R³ | R | mp (°C.) |
|---|---|---|---|---|---|
| | NMR(200MHz, D₂O)ppm: 1.23(1H, m), 1.52(1H, m), 2.10–2.45(4H, m), 3.35–3.70(3H, m), 4.05–4.25(1H, m), 5.27 (1H, dd, J=16, 6.8Hz), 6.03(1H, d, J=16Hz), 6.45–7.15(8H, m), 7.15–7.65(3H, m), 8.14(1H, d, J=8.2Hz) | | | | |
| 41-1 | —(CH₂)₂—OMe | 4'-F | H | Me | 132–135 |
| 41-2 | " | " | " | Na | — |
| | NMR(200MHz, D₂O)ppm: 1.25–1.40(1H, m), 1.50–1.70(1H, m), 2.26(2H, d, J=6.2Hz), 3.16(3H, s), 3.45–3.60(1H, m), 3.52(2H, t, J=6.0Hz), 4.03(2H, t, J=6.0Hz), 4.15–4.30 (1H, m), 5.44(1H, dd, J=16, 7.2Hz), 6.23(1H, d, J=16Hz), 7.20–7.40(4H, m), 7.53–7.65(1H, m), 7.70–7.85(2H, m), 8.26(1H, d, J=7.8Hz) | | | | |
| 42-1 | —(CH₂)₂—SMe | 4'-F | H | Me | oily |
| | NMR(200MHz, CDCl₃)ppm: 1.20–1.60(2H, m), 1.92(3H, s), 2.44(2H, d like, J=6.1Hz), 2.55–2.70(2H, m), 3.12(1H, s), 3.59(1H, s), 3.74(3H, s), 3.95–4.20(3H, m), 4.34(1H, bs), 5.51(1H, dd, J=16, 6.2Hz), 6.22(1H, d, J=16Hz), 7.10–7.35(4H, m), 7.45–7.85(3H, m), 8.51(1H, d, J=8.0Hz) | | | | |
| 42-2 | —(CH₂)₂—SMe | 4'-F | H | Na | — |
| | NMR(200MHz, D₂O)ppm: 1.30(1H, m), 1.58(1H, m), 1.77(3H, s), 2.26(2H, d, J=6.4Hz), 2.45–2.60(2H, m), 3.50(1H, bm), 3.85–4.05(2H, m), 4.15–4.35(1H, m), 5.42(1H, dd, J=16, 6.8Hz), 6.21(1H, d, J=16Hz), 7.20–7.40(4H, m), 7.50–7.85 (3H, m), 8.25(1H, d, J=8.0Hz) | | | | |
| 43-1 | —CH₂—CH=CH₂ | 4'-F | H | Me | 105–107 |
| 43-2 | " | " | " | Na | — |
| | NMR(200MHz, D₂O)ppm: 1.30(1H, m), 1.58(1H, m), 2.25(2H, d, J=6.2Hz), 3.50(1H, m), 4.23(1H, m), 4.39(2H, m), 4.71 (1H, d, J=17Hz), 5.09(1H, d, J=11Hz), 5.41(1H, dd, J=16, 7.0Hz), 5.60–5.85(1H, m), 6.18(1H, d, J=16Hz), 7.10–7.35 (4H, m), 7.50–7.85(3H, m), 8.25(1H, d, J=8.0Hz) | | | | |
| 44-1 | —(CH₂)₂—C₆H₄—CF₃ | 4'-F | H | Me | 144–146 |
| 44-2 | " | " | " | Na | — |
| | NMR(200MHz, DMSO)ppm: 1.08(1H, m), 1.37(1H, m), 1.70–1.90(1H, m), 1.90–2.10(1H, m), 2.80–3.00(2H, m), 3.75–4.20(4H, m), 5.47(1H, dd, J=16, 5.8Hz), 6.08(1H, d, J=16 Hz), 7.00–8.00(11H, m), 8.38(1H, d, J=7.4Hz) | | | | |
| 45-1 | —(CH₂)₂—F | 4'-F | H | Me | oily |
| | NMR(200MHz, CDCl₃)ppm: 1.20(2H, m), 2.44(2H, d like, J=6.1Hz), 3.22(1H, d, J=1.8Hz), 3.65(1H, d, J=2.6Hz), 3.73(3H, s), 4.09(1H, bm), 4.14(2H, dt, J=24, 4.9Hz), 4.35(1H, bm), 4.64(2H, dt, J=47, 4.9Hz), 5.52(1H, dd, J= 16, 6.2Hz), 6.20(1H, d, J=16Hz), 7.10–7.35(4H, m), 7.50–7.85(3H, m), 8.50(1H, d, J=7.0Hz) | | | | |
| 45-2 | —(CH₂)₂—F | 4'-F | H | Na | — |
| | NMR(200MHz, D₂O)ppm: 1.28(1H, m), 1.56(1H, m), 2.26(2H, d like, J=6.0Hz), 3.52(1H, m), 3.95–4.30(3H, m), 4.41 (1H, m), 4.65(1H, m), 5.32(1H, dd, J=16, 6.8Hz), 6.05(1H, d, J=16Hz), 7.10–7.70(7H, m), 8.09(1H, d, J=8.2Hz) | | | | |
| 46-1 | —(CH₂)₂CONMe₂ | 4'-F | H | t-Bu | 84–87 |
| 46-2 | —(CH₂)₂CONMe₂ | 4'-F | H | Na | 84–87 |
| | NMR(200MHz, D₂O)ppm: 1.33(1H, m), 1.56(1H, m), 2.26(2H, d, J=6.2Hz), 2.57(2H, t like, 7.4Hz), 2.82(6H, s), 3.52 (1H, m), 4.01(2H, t like, J=7.4Hz), 4.15–4.30(1H, m), 5.43(1H, dd, J=16, 7.0Hz), 6.23(1H, d, J=16Hz), 7.20–7.40 (4H, m), 7.50–7.65(1H, m), 7.70–7.85(2H, m) | | | | |
| 47-1 | —CHMe₂ | 4'-F | H | t-Bu | 118–119 |
| 47-2 | " | " | " | Na | — |
| | NMR(200MHz, D₂O)ppm: 1.15–1.70(2H, m), 1.41(6H, dd, J= 7.2Hz), 1.54–1.80(4H, m), 2.23(2H, d like, J=7Hz), 2.20–2.65(4H, m), 3.37–3.55(1H, m), 4.05–4.28(2H, m), 5.24 (1H, dd, J=16, 7Hz), 6.05(1H, d, J=16Hz), 7.16–7.45(4H, m) | | | | |
| 48-1 | —(CH₂)₂Me | 4'-F | H | t-Bu | 136–137 |
| 48-2 | —(CH₂)₂Me₂ | 4'-F | H | Na | 136–137 |
| | NMR(200MHz, D₂O)ppm: 0.70(3H, t, J=7Hz), 1.03–1.84(8H, m), 1.60–1.84(4H, m), 2.30(2H, d like, J=6Hz), 2.42–2.70(4H, m), 3.00–3.20(1H, bd), 3.52–3.77(3H, m), 3.87–4.08(1H, m), 4.10–4.28(1H, m), 5.17(1H, dd, J=16, 6Hz), 5.97(1H, d, J=16Hz), 7.02–7.27(4H, m) | | | | |

EXAMPLE 49-1 t-Butyl [3R,5S(E)]-7-[1,2-dihydro-3-(4-fluorophenyl)-2-propyl-1-oxo-4-isoquinolinyl]-3,5-dihydroxy-6-heptenoate The compound obtained by step 3 of Reference Example 49 was reacted and treated in the same way as in Example 1-1 to give the title compound as colorless crystals.

mp 117°–119° C. (from ethyl acetate-isopropyl ether-n-pentane).

IR$\nu_{max}^{Nujol}$cm$^{-1}$: 3400, 1720, 1690, 1645, 1595, 1230, 1150.

NMR(200 MHz, CDCl$_3$): 0.72(3H,t,J=7.4 Hz), 1.2–1.7(2H, m), 1.48(9H,s), 2.35(2H,d-like, J=6 Hz), 3.28(1H,s), 3.70–3.85(2H,m), 3.71(1H,s), 4.09(1H,b), 4.34(1H,b), 5.50(1H,dd,J=16,6.4 Hz), 6.20(1H,dd,J=16,1.4 Hz), 7.10–7.35(4H,m), 7.48–7.90(3H,m), 8.52(1H,dd,J-7.4,1.6 Hz).

Elemental Analysis for C$_{29}$H$_{34}$NO$_5$F: Calculated: C, 70.28; H, 6.91; N, 2.83. Found: C, 69.99; H, 6.87; N, 2.64.

$[\alpha]_D^{23°C.}$ +20.4 (c=1.045, CH$_3$CN).

EXAMPLE 49-2

Sodium [3R, 5S(E)]-7-[1,2-dihydro-3-(4-fluorophenyl)-2-propyl-1-oxo-4-isoquinolinyl]-3,5-dihydroxy-6-heptenoate The compound obtained by Example 49-1 was reacted and treated in the same way as in Example 1-2 to give the title compound as white powder.

IR$\nu_{max}^{KBr}$cm$^{-1}$: 3400, 1635, 1600, 1570, 1505, 1480, 1400 1220.

NMR spectrum data of this product are identical with that of the compound obtained by Example 16-2.

EXAMPLE 49-3

[4R,6S(E)]-6-{2-[1,2-dihydro-3-(4-fluorophenyl)-2-propyl)-1-oxo-4-isoquinolinyl]ethenyl}-4-hydroxy-3,4,5,6-tetrahydro-2H-pyran-2-one 1N-Sodium hydroxide (1 ml) was added to a solution of the compound (245 mg) obtained by Example 49-1 in ethanol (5 ml), followed by stirring at room temperature for 15 hours. The reaction mixture to which water was added was washed with diethyl ether. The aqueous layer was acidified with 2N-hydrochloric acid and extracted with ethyl acetate. The extract was washed with aqueous sodium chloride solution, dried over anhydrous magnesium and distilled to give carboxylic acid of the compound of Example 49-2 as colorless oily substance. A solution of 1-(3-dimethylaminopropyl)-3-ethylcarbodiimide hydrochloride (104 mg) was added to a solution of this product in dichloromethane (5 ml), followed by stirring at room temperature for 1.5 hours. The reaction mixture to which ethyl acetate was added was washed with water, dried over anhydrous magnesium sulfate and distilled to remove the solvent. The residue was subjected to a silica gel column chromatography using ethyl acetate-n-hexane to give the title compound (125 mg) as colorless crystals.

mp 158°–159° C. (from ethyl acetate-isopropyl ether)

IR$\nu_{max}^{Nujol}$cm$^{-1}$: 3420, 1725, 1625, 1590, 1570, 1230, 1150.

NMR(200 MHz, CDCl$_3$)ppm: 0.73(3H,t,J=7.2 Hz), 1.45–1.85(2H,m), 2.03(1H,d,J=3.0 Hz), 2.65(2H,dd-like,J=6.8,4.6 Hz), 3.65–3.85 (2H,m), 4.27(1H,m), 5.12(1H,m), 5.55(1H,dd, J=16,6.4 Hz), 6.28(1H,d,J=16 Hz), 7.10–7.35(4H,m), 7.50–7.85(3H,m), 8.52(1H,d,J=7.4 Hz).

Elemental Analysis Calculated: C, 71.24; H, 5.74; N, 3.32. Found: C, 71.11; H, 5.82; N, 3.16.

$[\alpha]_D^{23°C.}$ +51.2° (c=1.04, CH$_3$CN).

EXAMPLE 50-1

Methyl (3R*, 5R*)-7-[1,2-dihydro-3-(4-fluoro-2-methoxyphenyl)-2-(1-methylethyl)-1-oxo-4-isoquinolinyl]-3,5-dihydroxyheptanate Triethylamine (5γ) and 10% Pd-C (containing 50% water) (30 mg) was added to a solution of the compound (55 mg) obtained by Example 1-1 in methanol (10 ml). In an atmosphere of hydrogen gas, the mixture was stirred at room temperature for 2.5 hours. The catalyst was filtered out, and the filtrate was washed with methanol. The combined solution of the filtrate and the washings was distilled to remove the solvent, thereby giving the title compound (35 mg) as colorless crystals.

mp 138°–140° C.

IR$\nu_{max}^{Nujol}$cm$^{-1}$: 3300, 1730, 1640, 1610, 1505, 1280.

NMR(200 MHz, CDCl$_3$)ppm: 1.3–1.7(4H,m), 1.44(3H,d,J=7 Hz), 1.57(3H,d,J=7 Hz), 2.44(2H,m), 2.1–2.6(2H,m), 3.1(1H,m), 3.3(1H,m), 3.65(1H,m), 3.79(3H,s), 3.89(1H,m), 4.2(1H,m), 6.8(2H,m), 7.13(1H,m), 7.48(1H,m), 7.7(2H,m), 8.51(1H,d,J=9 Hz)

EI-MS m/z: 485(M+).

EXAMPLE 50-2

Sodium (3R*, 5R*)-7-[1,2-dihydro-3-(4-fluoro-2-methoxyphenyl)-2-(1-methylethyl)-1-oxo-4-isoquinolinyl]-3,5-dihydroxyheptanoate The compound obtained by Example 50-1 was reacted and treated in the same way as in Example 1-2 to give the title compound as white powder.

IR$\nu_{max}^{KBr}$cm$^{-1}$: 3400, 1640, 1605, 1590, 1575, 1500, 1450, 1410, 1330, 1280, 1190, 1150, 1100.

NMR(200 MHz, D$_2$O)ppm: 1.2–0.16(4H,m), 1.38(3H,d,J-6.4 Hz), 1.50(3H,d,J=6.4 Hz), 2.3(2H,m), 2.5(2H,m), 3.7(1H,m), 3.84(3H,s), 3.89(1H,m), 4.13(1H,m), 7.04(2H,m), 7.27(1H,m), 7.63(1H,m), 7.84(2H,m), 8.33(1H,d,J=8.2 Hz).

SI-MS m/z: 516(M+ +Na), 493(M+).

What is claimed is:

1. A compound of the formula (I)

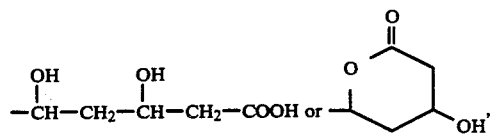

in which X is —CH=CH—, Y is

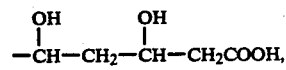

Z is an oxygen atom, R$^1$ is a C$_{1-10}$ straight or branched chain alkyl group or a phenyl-substituted C$_{1-2}$ alkyl group, R$^2$ is an optionally halogen-substituted phenyl group and the ring A is a benzene ring, or its C$_{1-6}$ alkyl ester or alkali metal salt.

2. A compound of the formula (I)

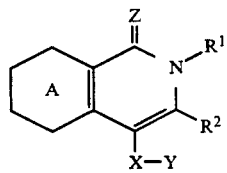

in which X is —CH=CH—, Y is

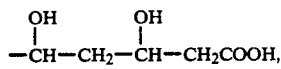

Z is an oxygen atom, $R^1$ is a $C_{1-10}$ straight or branched chain alkyl group or a phenyl-substituted $C_{1-2}$ alkyl group, $R^2$ is an optionally halogen-substituted phenyl group and the ring A is a cyclohexene ring, or its $C_{1-6}$ alkyl ester or alkali metal salt.

3. A compound of claim 1 or 2 in which the optionally halogen-substituted phenyl group is a fluoro-substituted phenyl group.

4. A compound of claim 1 or 2 which is 3R, 5S-configuration form or its racemate form.

5. A compound selected from the group consisting of [3R*, 5S*(E)]-7-[1,2-dihydro-3-(4-fluorophenyl)-2-(2-phenylethyl)-1-oxo-4-isoquinolinyl]-3,5-dihydroxy-6-heptenoic acid, [3R*, 5S*(E)]-7-[1,2-dihydro-3-(4-fluorophenyl)-2-methyl-1-oxo-4-isoquinolinyl]-3,5-dihydroxy-6-heptenoic acid, [3R*, 5S*(E)]-7-[1,2-dihydro-3-(4-fluorophenyl)-2-ethyl-1-oxo-4-isoquinolinyl]-3,5-dihydroxy-6-heptenoic acid, [3R, 5S(E)]-7-[1,2-dihydro-3-(4-fluorophenyl)-2-n-propyl-1-oxo-4-isoquinolinyl]-3,5-dihydroxy-6-heptenoic acid,

[3R*, 5S*(E)]-7-[1,2-dihydro-3-(4-fluorophenyl)-2-n-propyl-1-oxo-4-isoquinolinyl]-3,5-dihydroxy-6-heptenoic acid,

[3R*, 5S*(E)]-7-[1,2-dihydro-3-(4-fluorophenyl)-2-n-butyl-1-oxo-4-isoquinolinyl]-3,5-dihydroxy-6-heptenoic acid, [3R*, 5S*(E)]-7-[1,2-dihydro-3-(4-fluorophenyl)-2-i-butyl-1-oxo-4-isoquinolinyl]-3,5-dihydroxy-6-heptenoic acid, [3R*, 5S*(E)]-7-{1,2-dihydro-3-(4-fluorophenyl)-2-[2-(4-fluorophenyl)ethyl]-1-oxo-4-isoquinolinyl}-3,5-dihydroxy-6-heptenoic acid or

[3R*, 5S*(E)]-7-[3-(4-fluorophenyl)-1,2,5,6,7,8-hexahydro-2-n-propyl-1-oxo-4-isoquinolinyl]-3,5-dihydroxy-6-heptenoic acid, or its methyl, ethyl or tert-butyl ester, or lactone or sodium salt.

6. An inhibitory agent for the biosynthesis of cholesterol which comprises an effective inhibitory amount of a compound of the formula (I) in claim 1 or 2, or its ester or salt and a pharmaceutically acceptable carrier, diluent or excipient.

7. An inhibitory agent for the biosynthesis of cholesterol which comprises an effective inhibitory amount of a compound as defined in claim 5 and a pharmaceutically acceptable carrier, diluent or excipient.

* * * * *

UNITED STATES PATENT AND TRADEMARK OFFICE
CERTIFICATE OF CORRECTION

PATENT NO. : 5,189,043
DATED : February 23, 1993
INVENTOR(S) : Hideaki NATSUGARI et al.

It is certified that error appears in the above-indentified patent and that said Letters Patent is hereby corrected as shown below:

Column 58 (CLAIM 1), lines 50-55, please correct formula (I) as follows:

INCORRECT

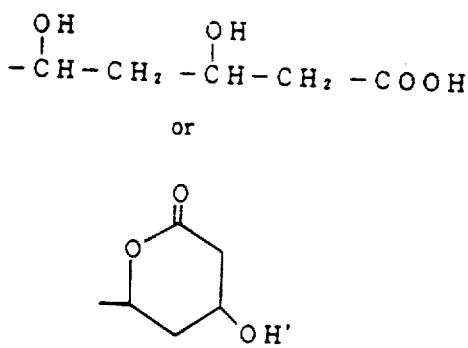

CORRECT

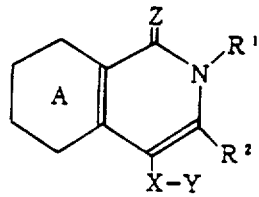

Signed and Sealed this

Tenth Day of May, 1994

Attest:

BRUCE LEHMAN

Attesting Officer  Commissioner of Patents and Trademarks